US007802183B1

(12) United States Patent
Essin

(10) Patent No.: US 7,802,183 B1
(45) Date of Patent: Sep. 21, 2010

(54) ELECTRONIC RECORD MANAGEMENT SYSTEM

(76) Inventor: Daniel J. Essin, 379 N. Encinitas Ave., Monrovia, CA (US) 91016

( * ) Notice: Subject to any disclaimer, the term of this patent is extended or adjusted under 35 U.S.C. 154(b) by 1020 days.

(21) Appl. No.: 10/150,709

(22) Filed: May 17, 2002

Related U.S. Application Data

(60) Provisional application No. 60/291,742, filed on May 17, 2001.

(51) Int. Cl.
  G06F 17/21 (2006.01)
  G06Q 90/00 (2006.01)
  G06F 17/30 (2006.01)
(52) U.S. Cl. .......................... 715/255; 715/234; 705/2; 705/3
(58) Field of Classification Search .................. 715/500, 715/500.1, 501.1, 513, 515, 764, 514, 520, 715/516, 201, 234, 209, 255; 704/1; 705/2, 705/3, 1, 4; 600/300
See application file for complete search history.

(56) References Cited

U.S. PATENT DOCUMENTS

| | | | | |
|---|---|---|---|---|
| 4,445,795 | A * | 5/1984 | Levine et al. .................. 400/63 |
| 5,146,439 | A | 9/1992 | Jachmann et al. |
| 5,267,155 | A * | 11/1993 | Buchanan et al. ........... 715/540 |
| 5,778,402 | A * | 7/1998 | Gipson ........................ 715/201 |
| 5,823,948 | A * | 10/1998 | Ross et al. ................... 600/300 |
| 5,832,450 | A | 11/1998 | Myers et al. |
| 5,915,240 | A * | 6/1999 | Karpf ............................. 705/2 |
| 5,924,074 | A | 7/1999 | Evans |
| 6,031,526 | A * | 2/2000 | Shipp ....................... 715/500.1 |
| 6,081,809 | A * | 6/2000 | Kumagai ............................ 1/1 |
| 6,182,029 | B1 * | 1/2001 | Friedman ........................ 704/9 |
| 6,289,513 | B1 * | 9/2001 | Bentwich .................... 717/106 |
| 6,304,848 | B1 * | 10/2001 | Singer ............................. 705/3 |
| 6,539,387 | B1 * | 3/2003 | Oren et al. ................... 707/100 |
| 6,684,188 | B1 * | 1/2004 | Mitchell et al. ................ 705/3 |
| 6,697,777 | B1 * | 2/2004 | Ho et al. ...................... 704/235 |
| 6,757,898 | B1 * | 6/2004 | Ilsen et al. ................... 709/203 |
| 6,871,179 | B1 * | 3/2005 | Kist et al. .................... 704/275 |
| 6,938,203 | B1 * | 8/2005 | Dimarco et al. ............. 715/513 |
| 6,993,708 | B1 * | 1/2006 | Gillig .......................... 715/234 |

(Continued)

OTHER PUBLICATIONS

*ChartWare™ User Guide*, Version 5.0, Sep. 1995, pp. 1-37.
Essin, D.J., Intelligent Processing of Loosely Structured Documents as a Strategy for Organizing Electronic Health Care Records, Meth. Inform. Med., 1993, pp. 27-30, vol. 32: No. 4.

(Continued)

*Primary Examiner*—Adam L Basehoar
(74) *Attorney, Agent, or Firm*—Christie, Parker & Hale, LLP

(57) ABSTRACT

An electronic record management system utilizes semi-structured documents that contain both authenticated partial texts created by an author and pointers to audio recordings that will be processed later by transcribers. The transcribed material is held in temporary storage until reviewed and approved by the author. When approved, the transcribed text may be combined with the original authenticated partial text to produce a final authenticated document. In addition, the record management system may further include a mechanism for assigning multiple context-dependent meanings to at least a portion of the information items included in a document. The record management system therefore allows a variety of encoding schemes to be automatically overlaid on each document. This creates opportunities to re-use the information for secondary purposes, such as preparing bills (such as Medicare bills) that must conform to arbitrary sets of rules.

39 Claims, 19 Drawing Sheets

U.S. PATENT DOCUMENTS

| | | | |
|---|---|---|---|
| 7,076,436 B1 * | 7/2006 | Ross et al. | 705/3 |
| 2002/0161795 A1 * | 10/2002 | O'Rourke | 707/500 |
| 2003/0066028 A1 * | 4/2003 | Payne et al. | 715/500 |
| 2004/0015778 A1 * | 1/2004 | Britton et al. | 715/500 |
| 2004/0024616 A1 * | 2/2004 | Spector et al. | 705/2 |
| 2004/0078217 A1 * | 4/2004 | Bacevice et al. | 705/2 |
| 2004/0243545 A1 * | 12/2004 | Boone et al. | 707/2 |
| 2005/0256746 A1 * | 11/2005 | Zaleski | 705/3 |
| 2007/0180368 A1 * | 8/2007 | Huber et al. | 715/523 |
| 2007/0192136 A1 * | 8/2007 | Lipscher et al. | 705/2 |

OTHER PUBLICATIONS

Essin, D.J., et al., An Information Model for Medical Events, Proceedings of the 18th Annual Symposium on Computer Applications in Medical Care, Nov. 1994.

Lincoln, T., et al., The Introduction of a New Document Processing Paradigm Into Health Care Computing, Cait White Paper, 1994, U.S.A.

Essin, D.J., Semantics from Loosely Structured Electronic Health Records, Meth. Inform. Med., vol. 32, 1993.

Chute, C.G., Clinical Classification and Terminology, The Journal of the America Medical Informatics Association, 2000, pp. 298-303, vol. 7 No. 4.

* cited by examiner

ELECTRONIC RECORD MANAGEMENT SYSTEM

CROSS REFERENCE TO RELATED APPLICATION

This application claims priority to U.S. Provisional Patent application Ser. No. 60/291,742, entitled "ELECTRONIC RECORD MANAGEMENT SYSTEM" filed on May 17, 2001 the content of which is incorporated herein by reference.

FIELD OF THE INVENTION

The present invention is generally related to data processing systems and more particularly relates to electronic record management systems.

BACKGROUND

Professionals are frequently required to document events that they have observed or in which they are participants. Depending on the situation and the circumstances, the documentation may all be created contemporaneously with the event, or it may be prepared later from notes or it may be dictated and transcribed. Typically, it is the responsibility of the professional to personally attest to the accuracy and completeness of the completed documents. Furthermore, it is typically the responsibility of the custodian of these documents to ensure their integrity.

For example, it is common in the healthcare field to combine contemporaneous and deferred documentation. In this instances the health care professional is ultimately responsible for attesting to the accuracy, completeness and authenticity of every document entered into a patient's medical record. Law enforcement and other professions involving inspection or oversight have a similar responsibility to produce credible contemporaneous documentation for good record management as well as to prevent or defend against claims of liability or violations of law.

As event documentation has become ever more detailed and complex, the need for automated processes for collecting, storing, transmitting, and retrieving information becomes more critical. Historically, hand-entered records are very brief and sometimes of limited value for future use, either because entries were illegible, used non-standard abbreviations, lacked sufficient detail, or were difficult to search. Because of the shortcomings of the paper-based record, electronic record management systems have been investigated for a number of years. Current electronic record management systems provide some advantages over traditional hard-copy records, but have not been widely adopted by the professional community.

Current attempts to develop database architectures capable of storing and retrieving medical record information have failed to reconcile user desires for maintaining a format of unstructured information with database requirements for highly structured data storage. In addition, voice recognition systems capable of generating text from human speech address the area of dictation but offer few improvements in the organization and management of event documentation.

SUMMARY OF THE INVENTION

In one aspect of the present invention an electronic record management system includes means for creating electronic documents having one or more headings that define context within which an event may be documented, means for creating one or more subheadings for at least one of the one or more headings and means for uniquely defining meaning of the one or more subheadings in accordance with the one or more headings.

BRIEF DESCRIPTION OF THE DRAWING

These and other features, aspects, and advantages of the present invention will become better understood with regard to the following description, appended claims, and accompanying drawings, where:

FIG. 8 is a screen capture illustrating a portion of the document creation process including the inclusion of a quantitative modifier and a qualitative modifier in accordance with an exemplary embodiment of the present invention;

FIG. 19 is a screen capture of a historical record containing compatible documents created by a variety of diverse users that may be displayed and searched for a variety of uses in accordance with an exemplary embodiment of the present invention.

DESCRIPTION OF THE INVENTION

An exemplary embodiment of the present invention provides a method and apparatus for taking a hierarchical collection (outline) of terminology (stored in a relational database) and using that collection to animate a computer application. The described exemplary application, when animated by a specific outline allows the user to create a new document that describes an event.

In accordance with an exemplary embodiment the document may be composed of elements that conform to a standardized programming language such as, for example, the extensible markup language (XML) specification. As is known in the art, XML is a markup language for documents containing structured information. Structured information contains both content (words, pictures, etc.) and some indication of what function that content performs.

For example, in an exemplary embodiment of the present invention, content in a section heading has a different meaning from content in a footnote, which means something different than content in a figure caption or content in a database table, etc. The advantages of the present invention may be best understood in the context of an exemplary record management system that utilizes any of a variety of user interfaces such as for example a medical record management system having a conventional user interface as illustrated in the screen captures shown in FIGS. 3-7.

One of skill in the art will appreciate however, that the present invention is not limited to medical record applications. Rather the present invention is equally applicable to a variety of applications that require the contemporaneous documentation of events that must be authenticated and protected to meet legal and/or statutory requirements. In addition, the present invention may be used in conjunction with any of a variety of user interfaces to provide robust event documentation and record management. Therefore, the illustrated user interface and medical record application or by way of example only and not by way of limitation.

Figure 1:
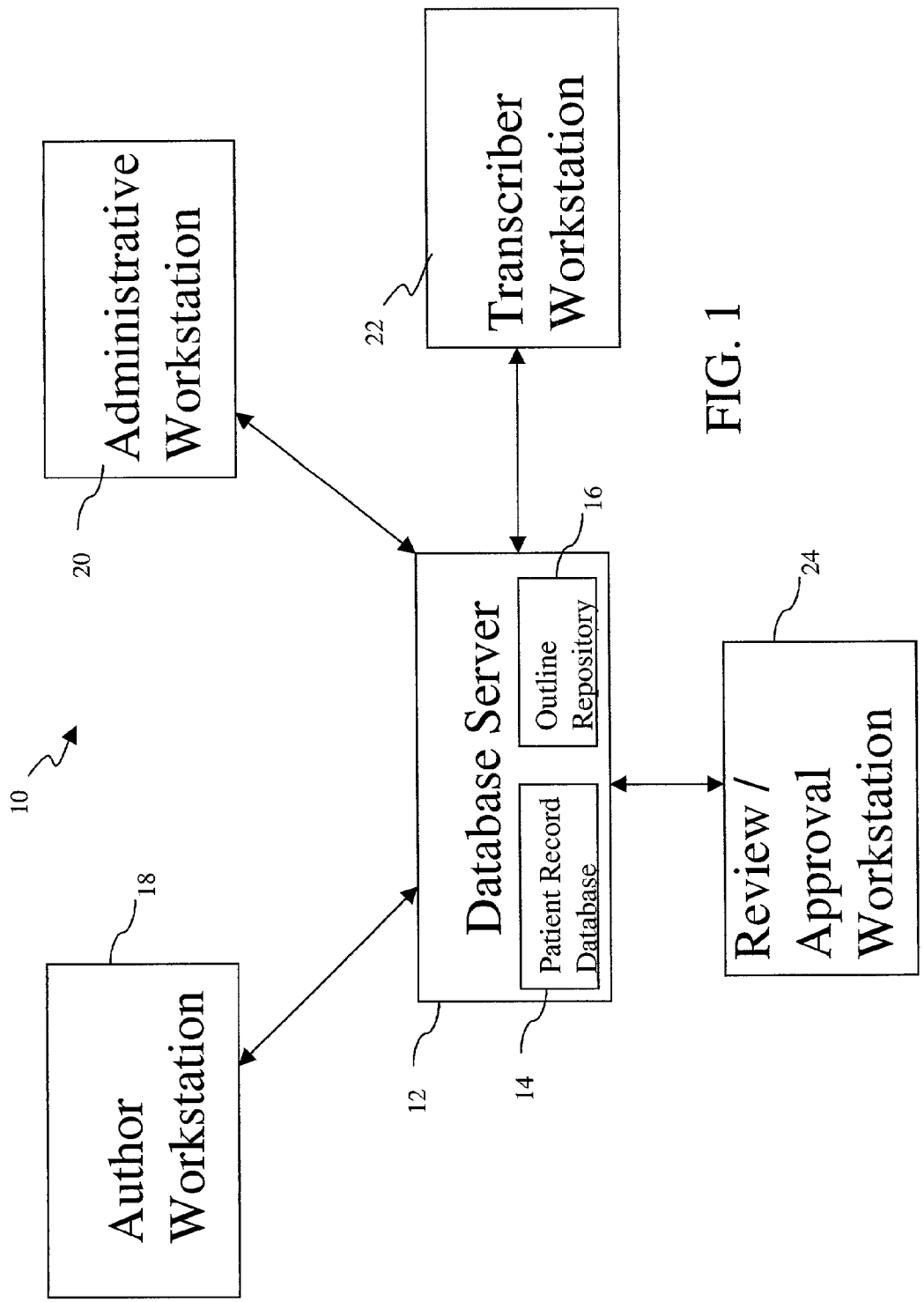
FIG. 1 is a functional block diagram of a record management system in accordance with an exemplary embodiment of the present invention.

FIG. 1 is a simplified block diagram of an exemplary medical record management system 10 comprising a database server 12 having a patient record database 14 and an outline repository 16. Initially, the described exemplary record management system may generate a skeletal document that may be utilized to document an event. In one embodiment an author or user may directly enter information into the skeletal document via an author workstation 18 coupled to the database server. Additionally, the author may generate narrative information that may be entered into the document on a deferred basis from a transcription workstation 22.

In the described exemplary embodiment dictated material may initially be electronically entered and stored in temporary storage within the database server until reviewed and approved by the author via an approval workstation 24. When approved the transcribed text may be merged with the original document to produce a final authenticated text that may be stored within the database server.

The described exemplary database server stores a document from the moment it is initiated, through the transcription and approval process. Thus, the described exemplary record management system may maintain complete control over documents because all of the facilities needed to complete the various stenographic and management tasks are self contained within the system. In addition, the database server may also retain completed documents for a designated or unlimited period of time. The described exemplary record management system therefore reduces the inefficiency that may result from transferring work from one system to another and reduces the likelihood of lost work.

In addition, the described exemplary record management system may maintain the veracity of the information throughout the process by the use of pass codes, PIN codes or other personal or biometric identifiers to control access to the document at every stage of the initiation and approval process. An exemplary embodiment of the present invention may utilize any one of variety of secure hash algorithms to generate a message digest at the time a record is created to provide verifiable documentation of the authenticity of each document.

Further, an administrator may review the status or process documents stored on the database server from an administrative workstation 20. The administrator may for example generate billing information from data contained within a document or review a document to ensure that all required action is being completed in a timely manner.

One of skill in the art will appreciate that the number and types of workstations may vary in accordance with the clinical setting of each application. In addition, the described exemplary record management system may be implemented using any appropriate computing device for each user workstation, e.g., 12. For example, the administrative workstation 20 may be a standard desktop personal computer while the author's workstation 14 may be a notebook-style computer or personal digital assistant.

In the described exemplary embodiment, the record management system is utilized as a medical record management system. However, the basic documentation and management system has other applications and can be used in other professions having similar documentation requirements. Therefore, the described exemplary medical record management system is by way of illustration only and not by way of limitation.

An exemplary record management system may often organize the information in a hierarchical outline fashion such as, for example, history, physical, assessment and plan. In accordance with an exemplary embodiment at least one of the divisions may be further divided into subdivisions that contain additional detailed information. The author or user may then document an event by entering a combination of quantitative information and free form narrative text into the outline.

In the described exemplary embodiment each of the major division of an outline establishes a context. Likewise, the subdivisions refine and subdivide the context and are therefore called micro-contexts. In addition, the information may take on a different meaning depending on which division of the outline it falls within.

Figure 2:
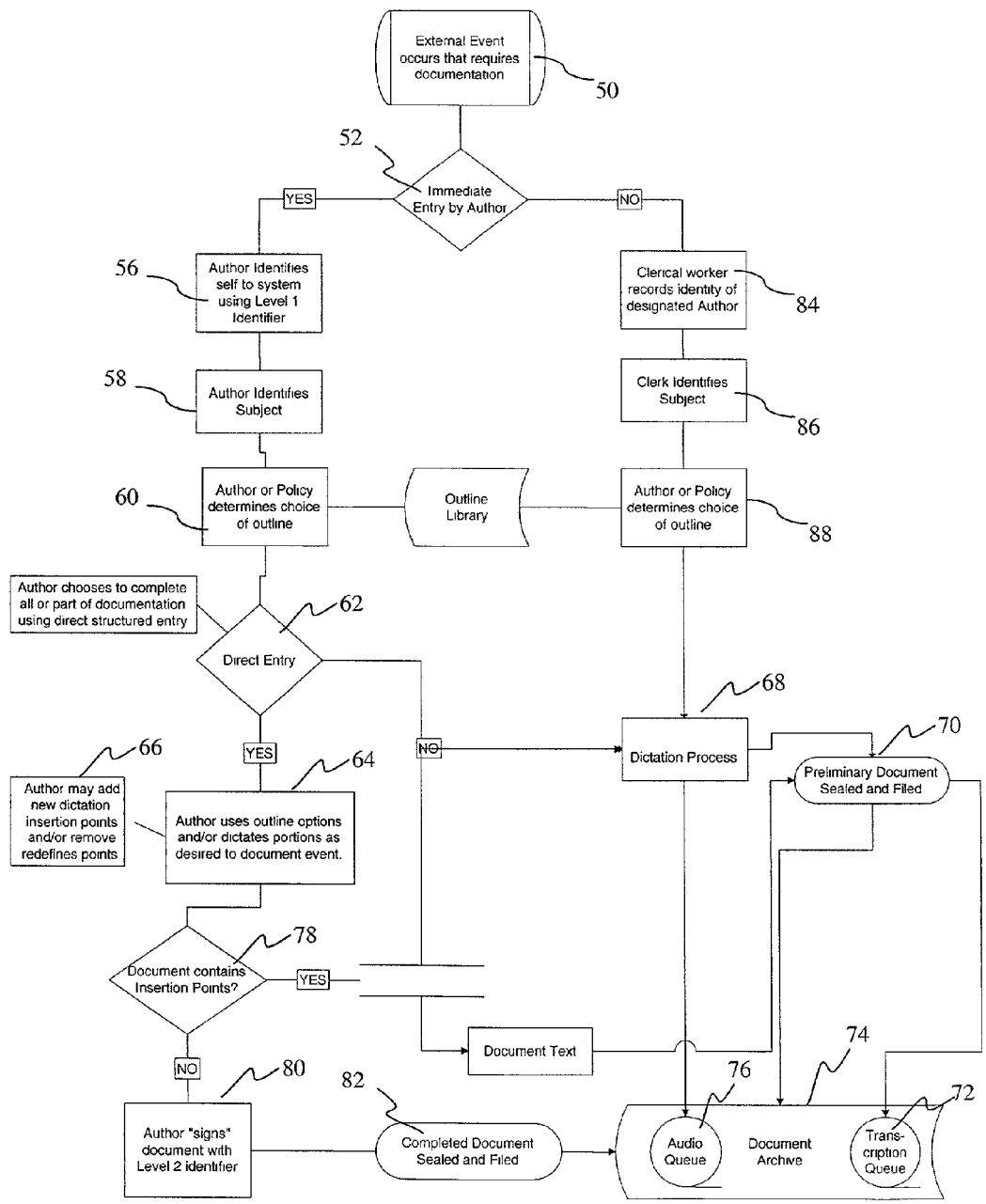
FIG. 2 is a flowchart graphically illustrating a process for initiating a new document in accordance with an exemplary embodiment of the present invention.

FIG. 2 is a flow chart illustrating an exemplary process for initiating a new document. When an external event occurs that requires documentation 50 the user or author may decide to immediately enter data to document the event 52 or to delay data entry. In the event the author decides to immediately create or edit a document an exemplary system may require an author to log onto the record management system by entering level one identifiers 56 such as for example a user name and password. The user may then identify the subject of the event to be documented 58.

Figure 3:
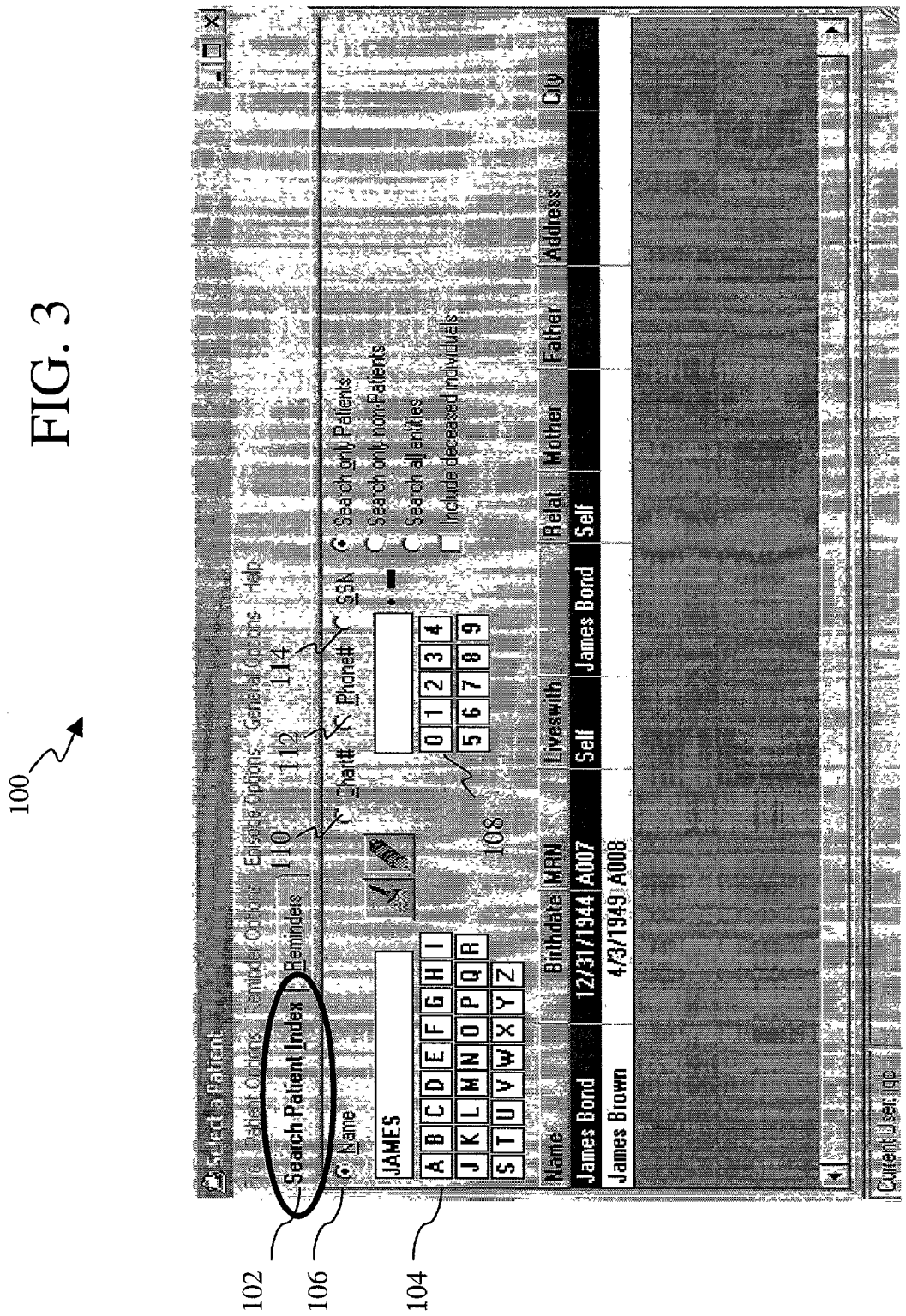
FIG. 3 is a screen capture of a conventional embodiment of an interface that allows a user to locate the records of an existing patient.

An exemplary system may then display a user interface 100 as illustrated in FIG. 3 that allows the user to create a new record or access an existing record to document the current event. In one embodiment an exemplary record management system may interface with a registration or billing system to automatically generate electronic documents that are uniquely identified. In this embodiment the electronic documents preferably include information that uniquely identifies the subject of the document.

The described exemplary record management system may therefore include a patient options feature that includes a search patient interface 102 having a keyboard 104 that allows the author to locate an existing record by entering the patients name 106. In accordance with an exemplary embodiment, the author may begin typing the patient's name which may be completed by an automatic quick fill feature that searches the record database and completes the patient's name when it can be uniquely identified. An exemplary search option interface may further include a numeric keyboard 108 that allows an author to locate an existing record in accordance with the medical record number 110, phone number 112, social security number 114, etc.

Figure 4:
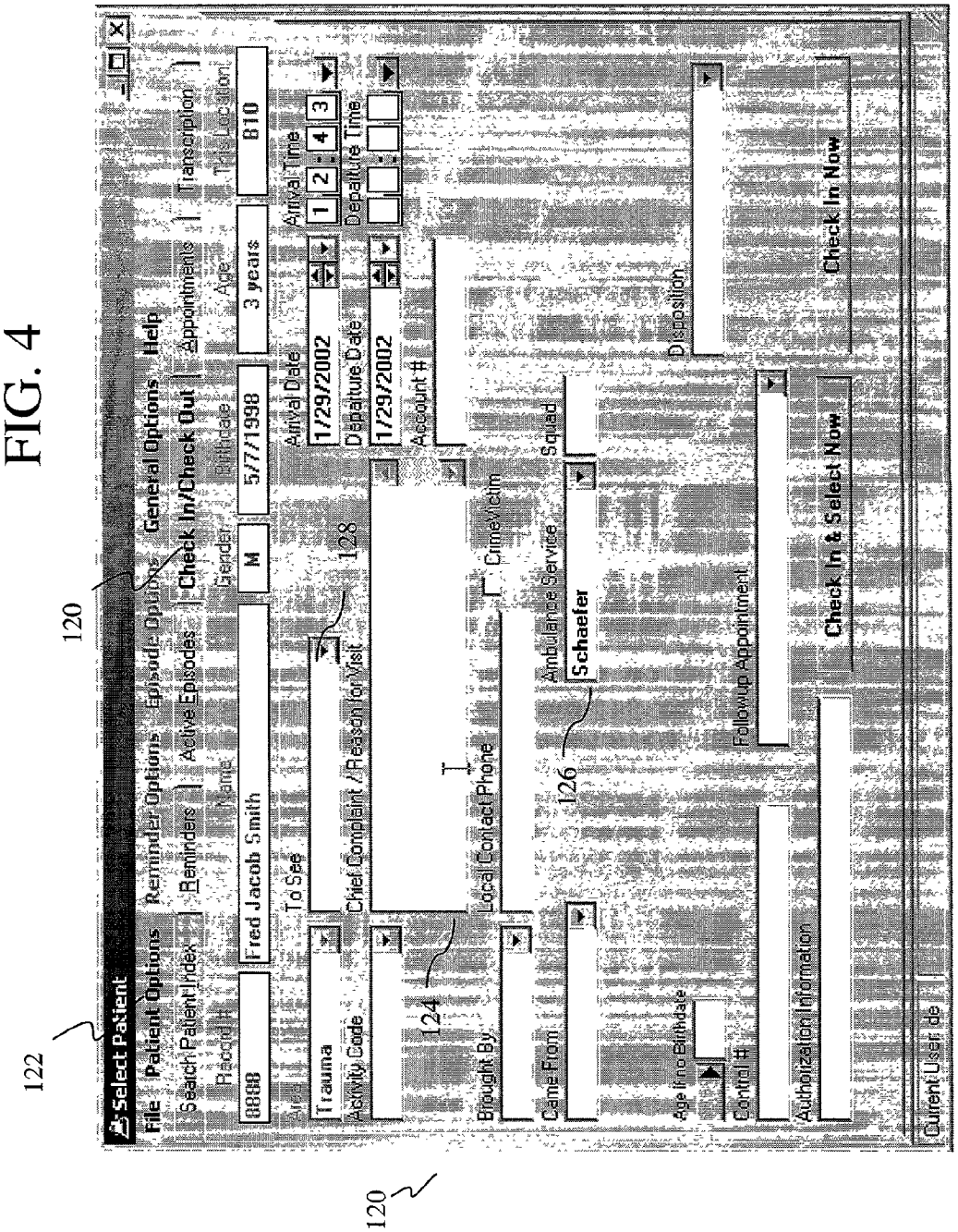
FIG. 4 is a screen capture of a conventional check in/check out interface for initiating an episode during which one or more events may be documented illustrating how it may be used to capture the information necessary to establish the situational contexts of one or more events.

Alternatively, the author may create a record to document the event from a check patient in/out interface 120 under a patient options feature 122 as illustrated in FIG. 4. This interface allows a user to enter personal information such as for example, the patient's name, address, phone number and birth date to identify the patient. The check-in interface further allows for the entry of information that documents the details surrounding the patient interaction. For example in one embodiment a user may enter the reason for the patient's visit 124, ambulance service used 126 if applicable, who the patient is here to see 128 as well as the point in time being described or documented and the time at which the document was initiated.

One of skill in the art will appreciate that the patient options feature may be adapted for a variety of different applications. For example, the search patient interface may be modified to locate a criminal investigation record by entering the name of a victim or alleged perpetrator. Similarly, the search patient interface could also be modified to locate a building inspection record by entering the address or owner of a building being inspected. Therefore, the described exemplary patient options interface is by way of example only and not be way of limitation.

Figure 5:
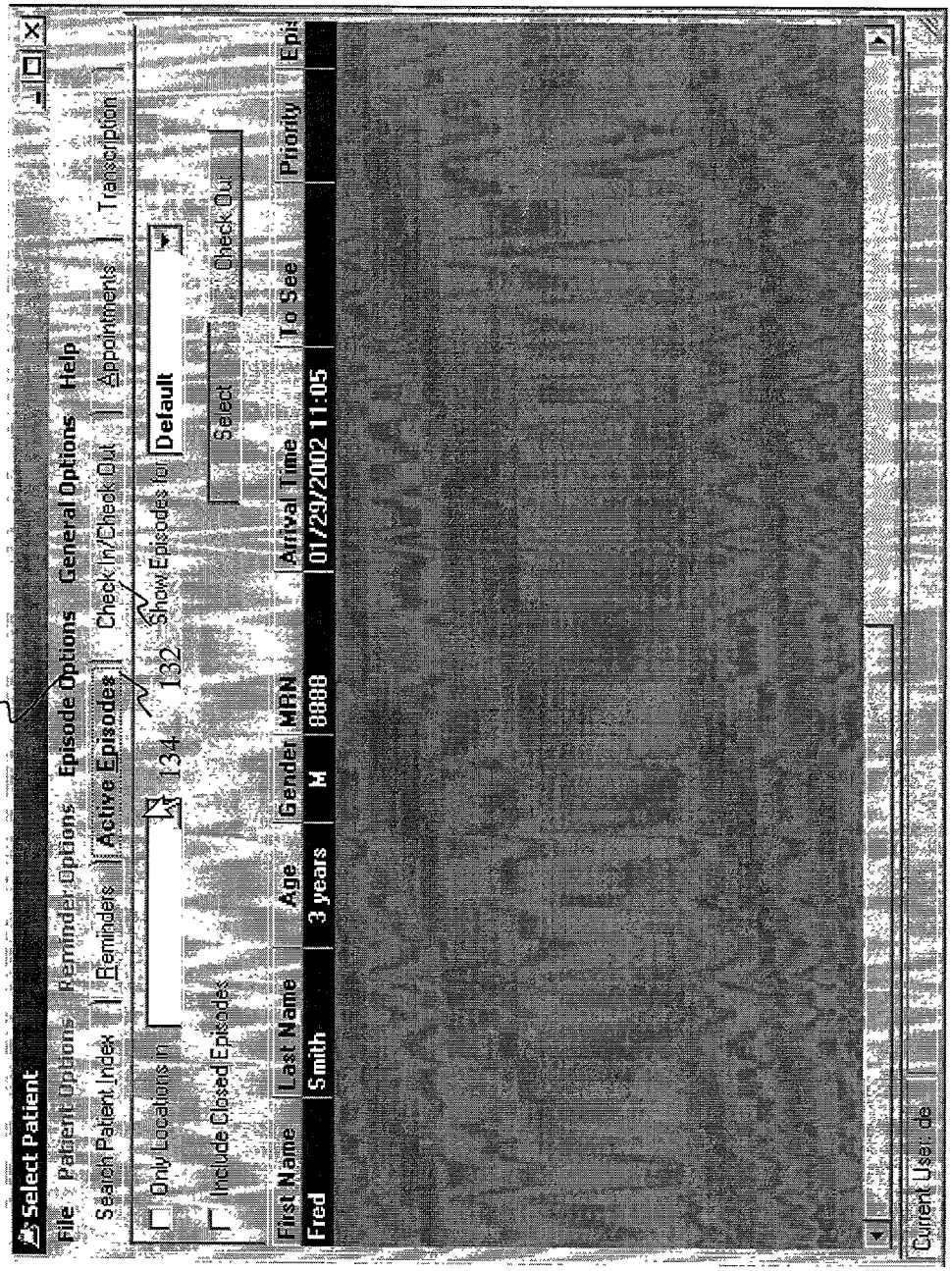
FIG. 5 is a screen capture of a conventional episode options interface that links the chart information from multiple sources for each patient visit.

In practice multiple parties may often complete various portion of an event documentation. For example, in a typical visit to a medical facility a nurse may document a patients vital signs, a doctor may document the history and physical examination and a dietician may document diet counseling. Referring to FIG. 5, the described exemplary record management system may therefore include an episode options feature 130 that links the chart information from multiple sources for each patient visit. In one embodiment a user may access a document associated with an active episode 134 to document a particular portion of an event.

Figure 6:
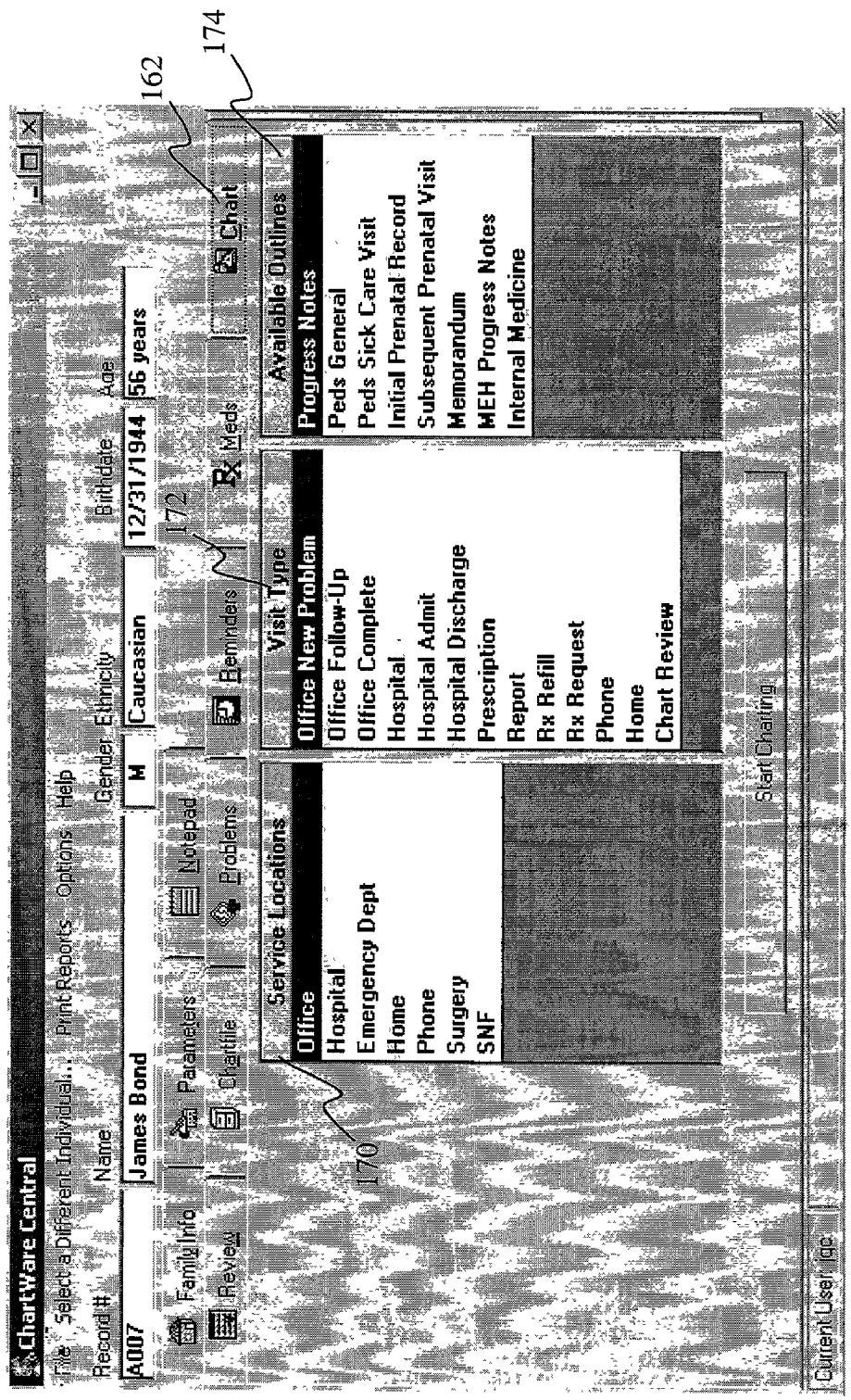
FIG. 6 is a screen capture of a conventional charting interface that allows for the selection of an outline that may be used to document the current event.

Returning to FIG. 2, a user may select an outline 60 from a charting option 162 on the individual patient interface (see FIG. 6). In the described exemplary embodiment a user may initiate the documentation process by identifying the service location 170 where the event occurred, the type of visit 172 and by selecting an outline 174 from numerous available outlines.

In the described exemplary embodiment a plurality of outlines may be generated and available for use under the charting feature. In accordance with an exemplary embodiment each outline defines a context of use, e.g. post-operative documentation of urological surgery. In the described exemplary embodiment, the available outlines may therefore be tailored to the practice of the individual user, to a particular event location, etc. The described exemplary outlines are therefore not limited to medical records but may be employed in a variety of other applications such as for example law enforcement, building inspection, polling administration, insurance claims investigation, etc.

For example, as illustrated in FIG. 6, a pediatrician's office may have outlines for general pediatric visits, sick care visits, initial prenatal visits, subsequent prenatal visits, etc. One of skill in the art will appreciate that the described exemplary record management system may be used to generate a variety of available outlines in accordance with the particular application. In addition, outlines may be modified during use by merging complete outlines or portions of outlines stored in the outline library on to the outline currently in use at a point chosen by the author or determined by an algorithm.

In addition, the described exemplary record management system may modify an outline during use in accordance with decision rules or programming logic stored within the outline. In one embodiment, the decision rules or programming logic may alter the options presented to the author, based on the content of the document at the time the rule is invoked or solely determined by the programming logic associated with a specific outline item.

Figure 7:
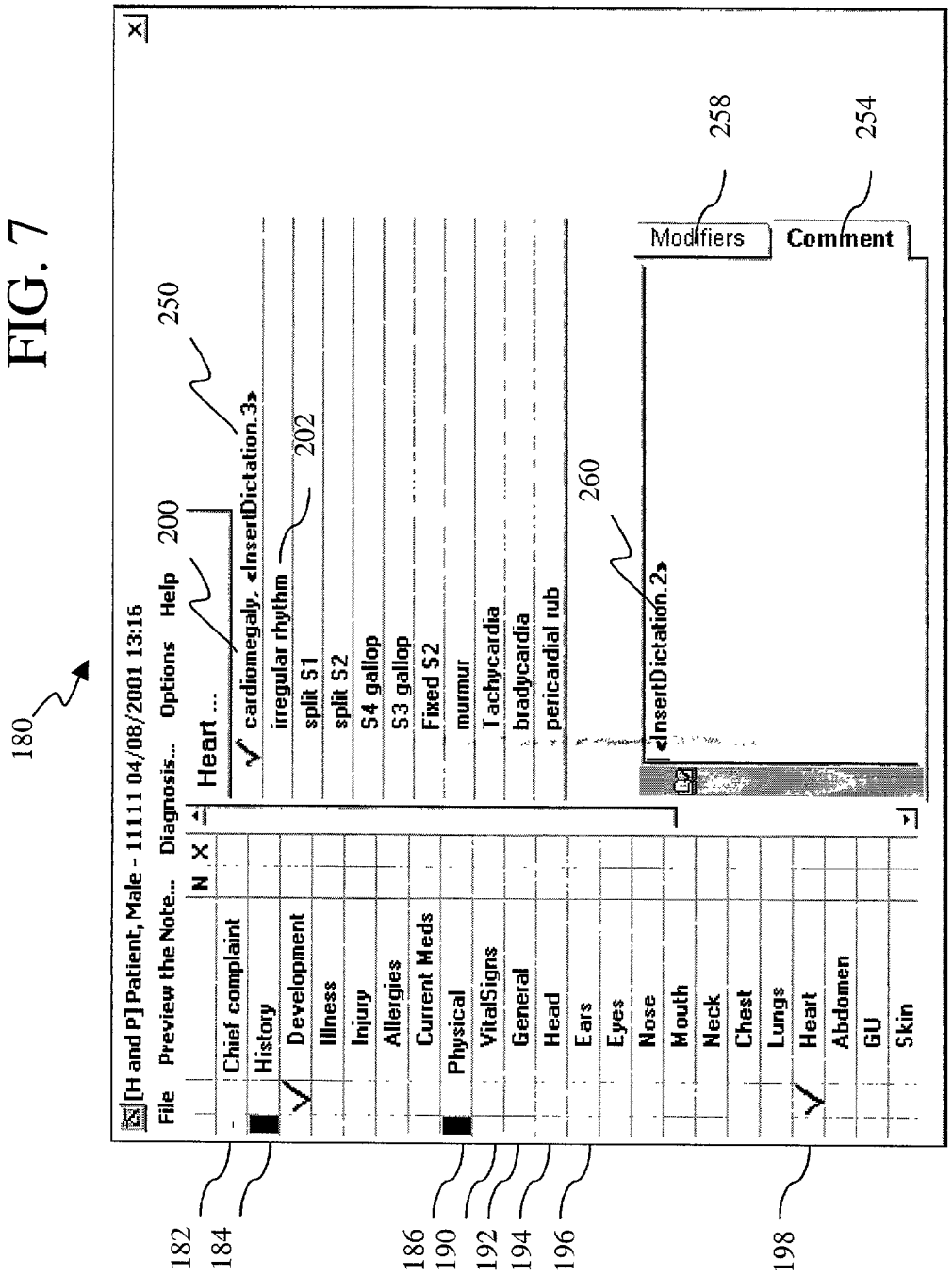
FIG. 7 is a screen capture of a portion of a conventional embodiment of a computerized document creation application that illustrates the way in which an outline item may be modified to allow for the inclusion of dictation insertion points within the outline.

Referring to FIG. 7 an exemplary outline may organize the information in a hierarchical outline fashion that leads the user through the event. For example, a general practitioner may have a general purpose outline 180 that includes the chief complaint 182, history 184, physical examination 186, assessment and plan (not shown).

In accordance with an exemplary embodiment at least one of the divisions may be further divided into subdivisions or micro-contexts that contain additional detailed information. For example, the physical examination context or division 186 may be further divided to include a variety of sub-divisions or primary micro-contexts such as for example vitals 190, general 192, head 194, ears 196, etc. that lead the physician through a typical physical examination.

In accordance with an exemplary embodiment an outline may be defined with additional granularity by incorporating a variety of micro-context subdivisions. For example, a heart micro-context 198 may receive multiple content items including a variety of common diagnoses such as cardiomegaly 200, irregular rhythm 202, etc. that a physician may utilize when performing a physical examination on a patient's heart. The items selected will then acquire the heart micro-context and have their subsequent meaning appropriately defined.

Returning back to FIG. 2, the described exemplary record management system allows a user to create documents that contain both quantitative and narrative information. Therefore, an author may choose to complete all or part of an event documentation using direct structured data entry 62.

Figure 8:
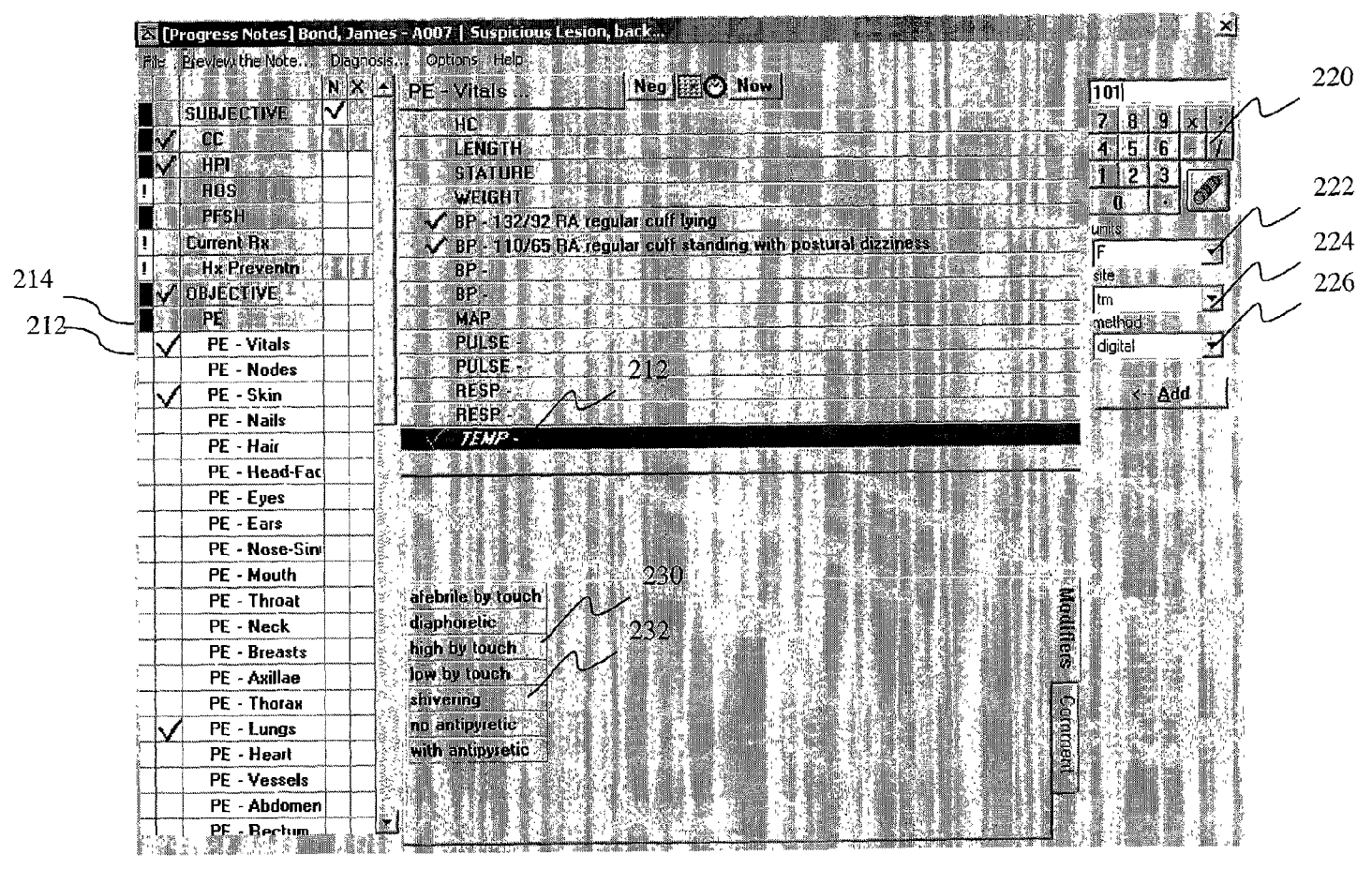

For example, referring to the outline of FIG. 8, a user may utilize a quantitative modifier to document a patient's temperature 210 under the vitals micro-context 212 of the physical examination primary micro-context 214. The described exemplary embodiment may include a numeric keypad 220 for entry of an actual numeric temperature as well as inputs for predefined attributes such as units 222, site 224 where temperature taken, method 226, etc. An exemplary outline may further include a qualitative modifier such as high by touch 230 shivering 232 etc. that further document the selected information item i.e. temperature in this example.

A user may also dictate portions of an examination, as desired, to document the event. In accordance with an exemplary embodiment a user may add new dictation insertion points to the outline or remove or redefine existing dictation insertion points that were included in the stored outline to identify where in the document dictated text should be added. The described exemplary record management system may then generate an XML document with dictation elements added to the document at each point where dictation was indicated.

For example, referring back to the outline illustrated in FIG. 7, the user has marked the cardiomegaly subdivision 200 of the heart micro-context 198 of the physical examination primary micro-context with an insertion point for supplemental dictation 250. The user has also marked the comment portion 254 of a qualitative modifier 258 for the heart micro-context with an insertion point for supplemental dictation 260.

Referring back to FIG. 2, the user may generate narrative text as desired to document the event 64. In the described exemplary embodiment the user may add dictation insertion points or remove dictation insertion points as desired 66. The user may then follow a standardized dictation process 68 to generate a preliminary document 70 that may be sealed to prevent unauthorized alteration of the originally document. For example, in one embodiment the described exemplary record management system may utilize a secure hash algorithm to generate a message digest at the time a record is created. The described exemplary record management system may then utilize the message digest during generation of a digital signature for the record. An exemplary record management system may also utilize the secure hash algorithm to compute a message digest for the received version of the record during the process of verifying the signature. Any change to the record will result in a different message digest, and the signature will fail to verify, indicating that an unauthorized alteration of the document may have occurred.

In the described exemplary embodiment the sealed document may then be stored in a transcription queue 72 of a document archive 74. The audio text may be stored in an audio queue 76 in the document archive for subsequent transcription and merger into the outline.

In accordance with an exemplary embodiment, if narrative documentation is not used as indicated by the absence of dictation insertion points, the user may sign the document with a level two identifier 80 such as for example a personal identification number. The portions of the document that are directly entered may then be sealed with a digital signature 82 and constitute a fully authenticated and usable but preliminary document.

Likewise, if direct data entry is not used, an author may generate narratives in accordance with a dictation process 68 to document the event. In this instance the narrative text may be stored in an audio queue in a document archive for subsequent transcription. The preliminary document having the transcription and insertion points may again be sealed and stored in a transcription queue in a document archive for subsequent merger with the transcribed text.

If the author is not going to immediately enter documenting data, a clerical worker may record the identity of the author 84 and identify the subject 86. An outline may again be selected in accordance with a particular policy or in accordance with the author's instructions 88. The author may then generate narrative text or dictation to document the event in accordance with standardized dictation insertion points. The narrative text may be stored in an audio queue in a document archive for subsequent transcription. The preliminary outline with dictation insertion points may again be sealed, stored in a transcription queue in a document archive for subsequent merger with the transcribed text.

In the described exemplary embodiment, an outline is completely customizable. A user may identify the requirements for coding and abstracting as well as the coding scheme required for each prior to the generation of an outline. For example, third-party payors and regulatory agencies often require that most healthcare episodes be abstracted and described in summary fashion using a coding scheme that they specify.

Many coding schemes are in wide use today and are suitable for this purpose. For example, the international classification of diseases (ICD) from the World Health Organization, the current procedural terminology (CPT) from the American Medical Association and the systematic nomenclature for medicine (SNOMED) from the College of American Pathologists (CAP) are just a few of the currently available coding schemes that may be utilized to document primary diagnosis or prescribed medical procedures.

Figure 9:
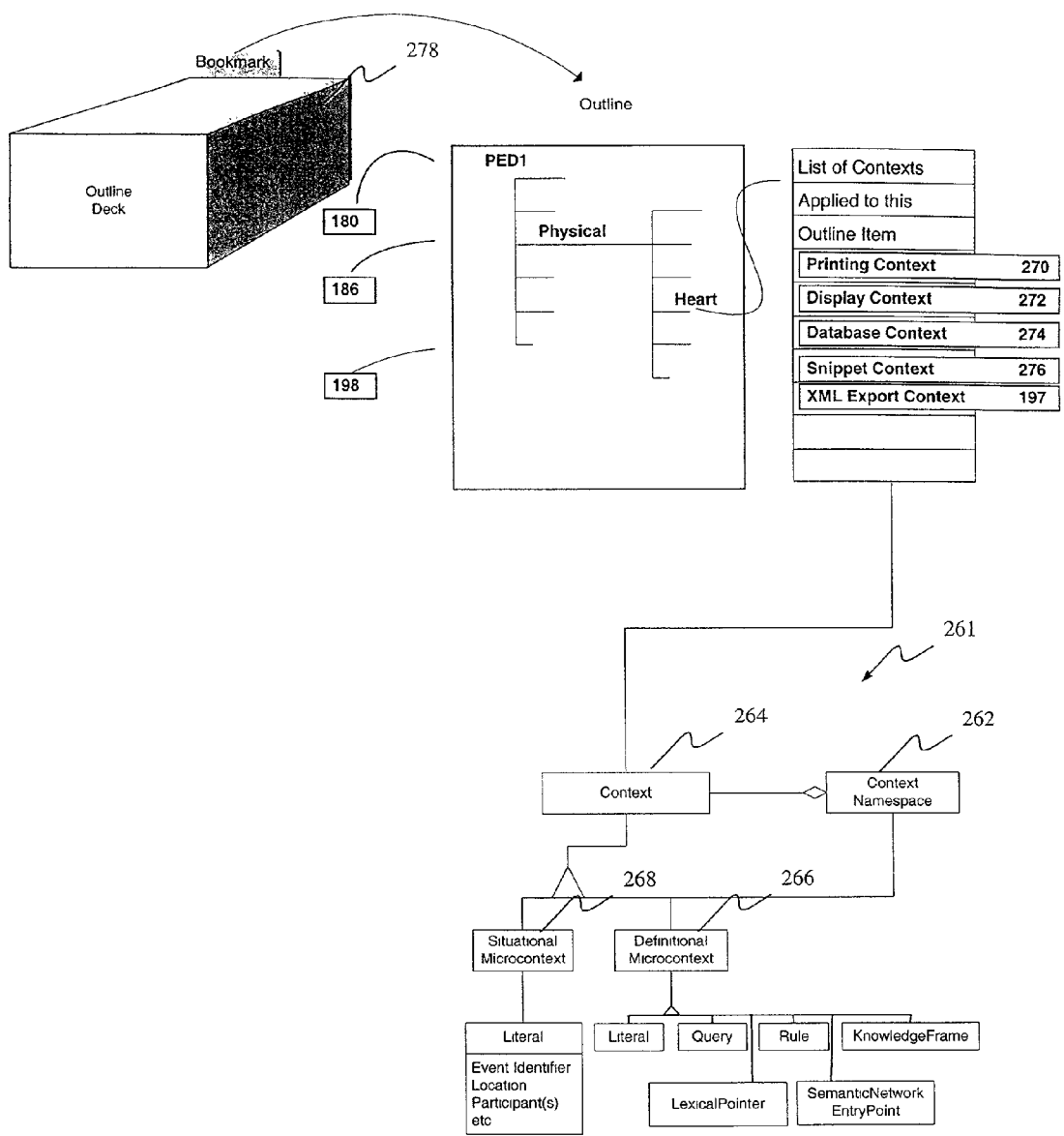
FIG. 9 is a graphical illustration of the assignment of a plurality of micro-contexts to an outline item in accordance with an exemplary embodiment of the present invention.

Therefore, the described exemplary electronic record management system allows for the assignment of micro-contexts to each section of the documentation outline to accommodate each coding requirement. The meaning, usually in the form of a specific coded value, may then be assigned to each context. For example, FIG. 9 graphically illustrates an exemplary process for linking a plurality of contexts to an outline item. For example, a plurality of context or micro-contexts may defined the heart context 198 of the physical examination primary context 186 in a pediatric outline 180.

In the described exemplary embodiment an outline may include a variety of universally applicable supplemental contexts such as, for example, a printed category label 270 that determines what headings are printed when output is generated, a display category label 272 that determines what headings appear on the screen or a database category value 274 that determines how informational items are named when stored in the database. In addition, the primary context may reference a code snippet 276 that further subdivides the primary context. The primary micro-context may further include an XML export tag 197.

One of skill in the art will appreciate that any number of contexts may be assigned or linked to a particular outline item. For example, an exemplary context object model 261 is illustrated wherein each of the context is stored in a hierarchical context namespace 262 for linking to an outline item. In an exemplary embodiment, the namespace nomenclature allows for the association of sub-groupings within sub-groupings within groupings etc. The namespace nomenclature therefore provides an understanding of the associations and groupings of related contexts.

In one embodiment the contexts may be either a definitional context 266, a situational context 268 or another context 264 providing a hierarchy since a context may contain a context. An exemplary situational context may comprise a template that has detail added when used. For example, in one embodiment the added details may vary in accordance with users or participants, location, service rendered etc. Definitional contexts on the other hand are defined in advance. In an exemplary embodiment the meaning of a given context may be defined by any of a variety of techniques.

For example, a micro-context may be given a literal value such as a billing code or diagnosis code. Alternatively, a context may be defined an indirect reference to a stored data item or from a database query that derives meaning from manipulating specified data elements that are external to the documentation event.

In addition, a given context may also be defined by an indirect reference to a rule such as a block of computer instructions which, when executed, assigns a meaning value. Similarly, a context may be defined in accordance with an indirect reference to a knowledge frame that assigns a complex meaning based on the slots defined for the frame and the current contents of the slots. Likewise the meaning of a given context may be defined by an indirect reference as a pointer into an externally defined lexical schemes or a semantic network or by creating an internal semantic network by using frames to define the nodes and by making indirect reference from node item to node item within the outline database.

In accordance with an exemplary embodiment a deck of customized outlines 278 may be compiled and stored on the database server. In one embodiment the individual outlines may be searched by title, area of use, etc. Alternatively, commonly used outlines may be book marked or tabbed in a user interface to provide ready access to these commonly used outlines for a particular individual or by location, service rendered, etc.

Figure 10:
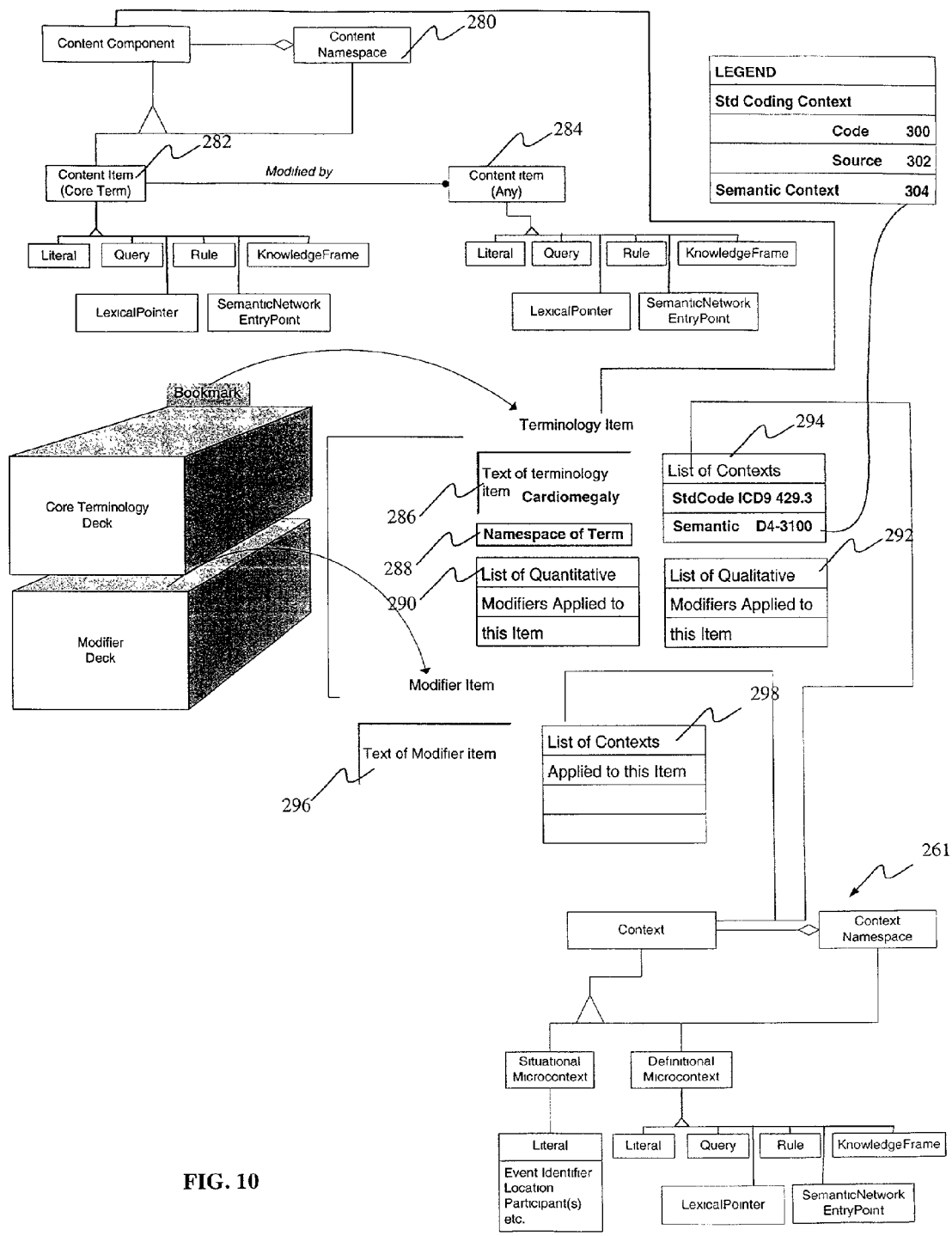
FIG. 10 is a graphical illustration of a portion of the process of generating stored vocabulary terms and their associated micro-contexts that may be utilized to when assigning micro-contexts to outline items as illustrated in FIG. 9 in accordance with an exemplary embodiment of the present invention.

FIG. 10 graphically illustrates the structure and generation of a core terminology deck and a modifier deck that provide the content that exists in a given context. The object model for content components largely replicates the object model for used to define context except that the content object model is all definitional. For example, the described exemplary content object space utilizes a content namespace 280 that is divided into two components comprising core terminology content items 282 and supplemental content items 284.

In an exemplary embodiment core terminology content items comprise those items that are displayed by the outline for inclusion in the final document, cardiomegaly for example. Supplemental content comprises modifiers that may be used to modify 286 or refine a core term that is being used. In an exemplary embodiment the content items may again be defined in accordance with literal values, pointers into lexical schemes etc as previously discussed with respect to context definitions.

In an exemplary embodiment, a terminology item may be analogously viewed as a card having a text box for the text of the term 286 in this case cardiomegaly along with a definition of the namespace of the term 288. In an exemplary embodiment a terminology card may comprise a plurality of list boxes including a list box for linkage to quantitative modifiers 290 and a list box for linkage to qualitative modifiers 292 as well as a list of contexts 294 that may be pre-associated with this term. In an exemplary embodiment of the present invention the pre-associated context may comprise the common coded values including the code value 300, the source 302 and if desired a semantic context 304 for a particular term.

For example, in the illustrated example, a standard coding micro-context is assigned to the heart term cardiomegaly. In that context the ICD9 diagnosis code is "429.3". In addition a semantic micro-context 304 such as, for example, SNOMED D4-3100 for congenital heart disease not otherwise specified may also be defined for the item. In addition, other contexts may be defined in accordance with links context items in the context object model 261 but are not illustrated in this view.

In an exemplary embodiment, modifier items may also be analogously viewed as index cards having a box for inserting the modifier text 296 and a list of associated context 298.

In accordance with an exemplary embodiment, an outline may therefore be generated to include links to the coding micro-contexts that define the meaning of each of the informational items. During the document creating process, the various codes, or pointers to them, are incorporated into the document as the author interacts with the outline. After documents are created from the outlines, the described exemplary record management system may automatically extract coded information from each document.

In practice, few terms have a definitive meaning independent from the context in which it is used. For example, an entry of hypertension in a patient's medical chart may correspond to a given diagnosis code in the context of the billing diagnosis. However, in the context of the medical assessment it may mean that the patient has a condition that is associated with hypertension, which must therefore be ruled out. At the same time, the entry of hypertension may mean that the entry is a medical history item, in the context of determining a Medicare evaluation and management code.

Therefore, the described exemplary record management system may assign different meaning to a given information item depending on which division of the outline the item falls within. In accordance with an exemplary embodiment the meaning of a micro-context may therefore be derived from the hierarchy present within the outline.

In addition, in the described exemplary embodiment supplemental micro-contexts and meanings may be given to outline items to assign a meaning for a given use. For example, in an exemplary embodiment of the present invention, a set of coding micro-contexts may be used to assign a meaning to each element of each outline in the context of the Medicare billing rules. The described exemplary record management system may then automatically calculate Medicare charge codes tallying the points in the various categories defined by the rules and then select the appropriate charge code.

For example, in one embodiment, each element of the outline may include metadata, by way of the micro-context, to describe and/or resolve the context in which the event is occurring such as Physical Examination, Pertinent Family History, etc. The described exemplary record management system may utilize metadata definitions to link or cross-reference the parent item with an unlimited number of uni-axial or multi-axial coding schemes. In an exemplary embodiment the metadata may include key attributes that may be used to match the characteristics of a specific event, such as visit type, service location, facility, organization, department, and division with a definition of how the item should be evaluated.

The described exemplary record management system may be extended to include item-associated pointers to the metadata along with the other data that is saved for each selected item. The information about the defined micro-contexts and associated meanings may be stored in the database and retrieved when necessary to ascertain the meaning of an item or the information about the additional micro-contexts and their associated meanings may be incorporated directly into the structured documents as they are created.

In actual practice, there may be many other groups and individuals, in addition to billing personnel that need to re-use information contained in a medical record. Most of these opportunities for re-use also require that different meanings be assigned to the same observations. For, example, it may be the case that the information is being used in a different context and therefore takes on a different meaning. Similarly there may be a need to group the information at a different level of granularity for the purpose of aggregating similar items or differentiating between items that are superficially similar.

The described exemplary record management system provides a general framework for placing a single informational item in multiple contexts and assigning a meaning that is to be inferred in each context. In addition, the assignment of a particular meaning in a given context at the time the outline is generated allows for the automation of data re-use for a variety of different purposes. To make the assignment of the additional meanings post hoc as is conventionally done requires human intervention to read the text and interpret the meaning in each context.

The described exemplary record management system may also provide a system for efficiently processing dictated portions of an outline. An exemplary transcription process is graphically illustrated in the flow chart of FIG. 11. A transcriber may first log onto the system by entering a login identification and a password 400. An exemplary record management system may present the transcriber with a task list 402 from the transcription queue 404 that may include all documents in need of transcription or some subset thereof.

Figure 12:
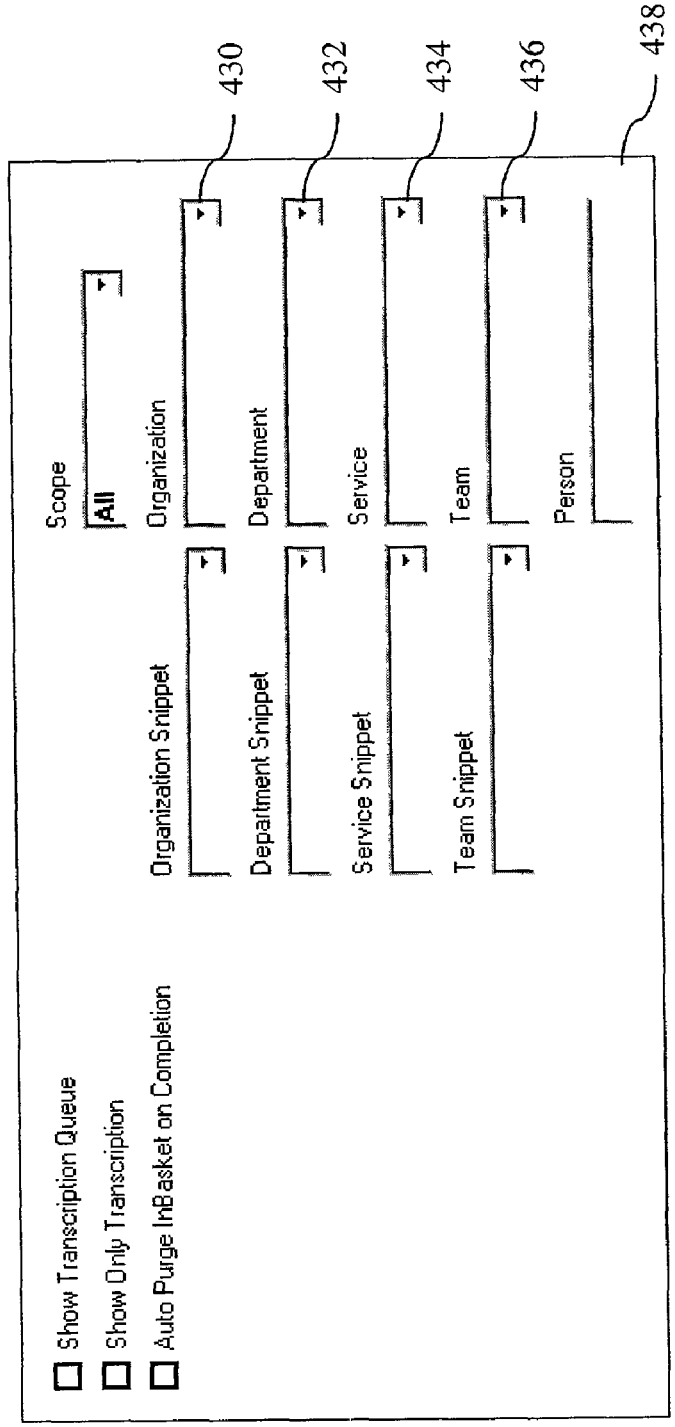
FIG. 12 is a screen capture illustrating the hierarchical categorization of audio documents that may be utilized to create virtual queues in the transcription queue to control the distribution of work to individual transcribers or transcription stations in accordance with an exemplary embodiment of the present invention.

For example, in one embodiment an exemplary record management system may categorize documents in accordance with the hierarchical structure of the originating organization to control the distribution of transcription tasks to individual transcribers or transcriber workstations. In one embodiment when a document is created it may be categorized in accordance with one or more of a variety of factors including initiating organization 430, initiating department 432, initiating service 434, initiating team 436 or initiating person 438 (see FIG. 12).

In an exemplary embodiment a virtual queue may be created in the transcription queue for each level in the hierarchy. In an exemplary embodiment, the number of queues may be dynamic and may be determined in accordance with the depth and breadth of the hierarchy that is defined. The described exemplary record management system may then control the distribution of documents to individual transcribers or individual transcription workstations by restricting access to the virtual transcription queues.

Figure 13:
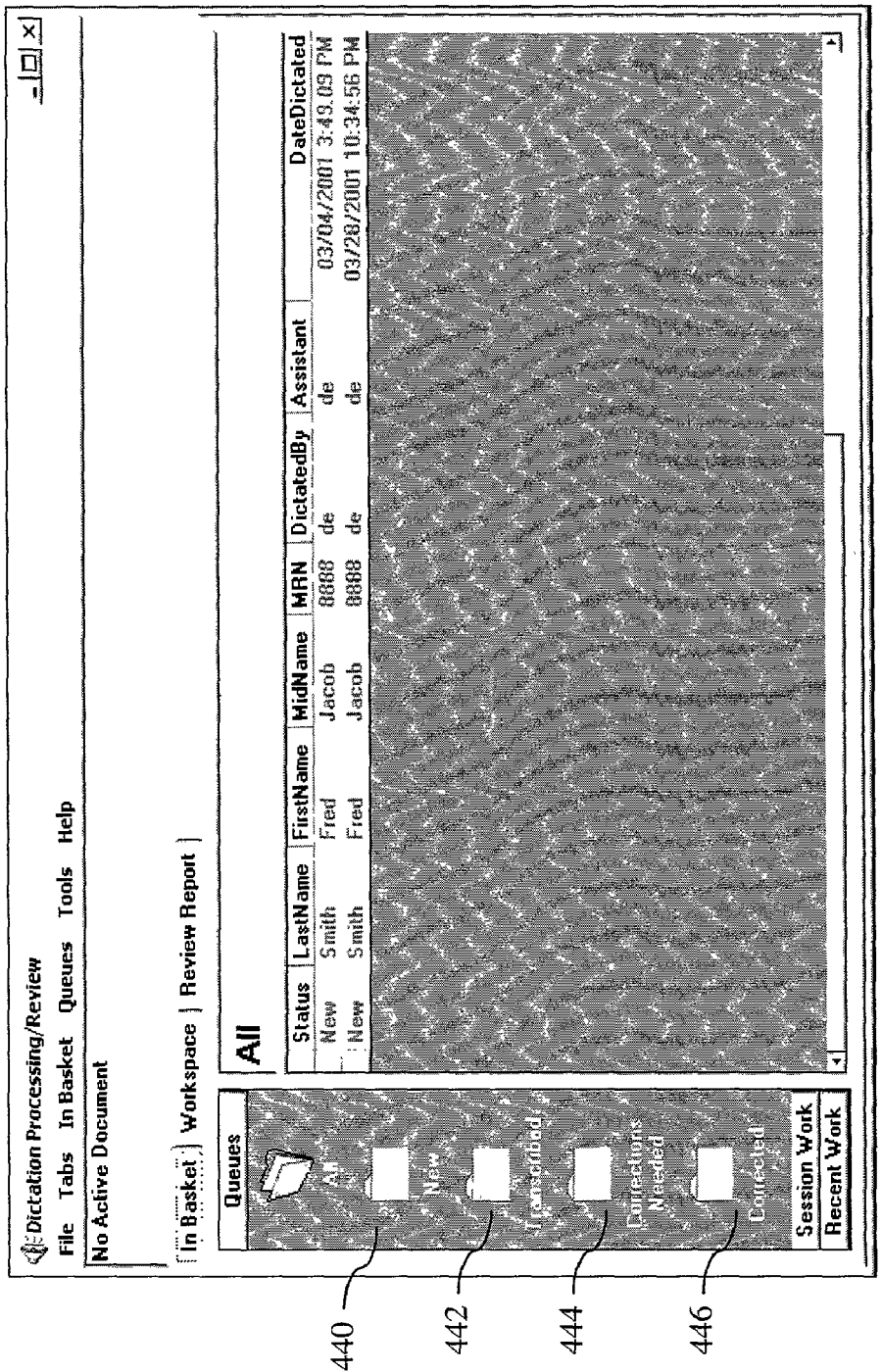
FIG. 13 is a screen capture illustrating a transcriber interface having virtual queues storing documents in accordance with the various stages of the transcription workflow process in accordance with an exemplary embodiment of the present invention.

In addition, each virtual queue may be subdivided in accordance with the various stages of the transcription workflow process. For example, each transcription queue may be subdivided into sub-queues for new work 440, work that has been transcribed but not reviewed 442, work that has been reviewed and returned for correction 444 and work that has been corrected 446 as illustrated in FIG. 13.

Figure 14:
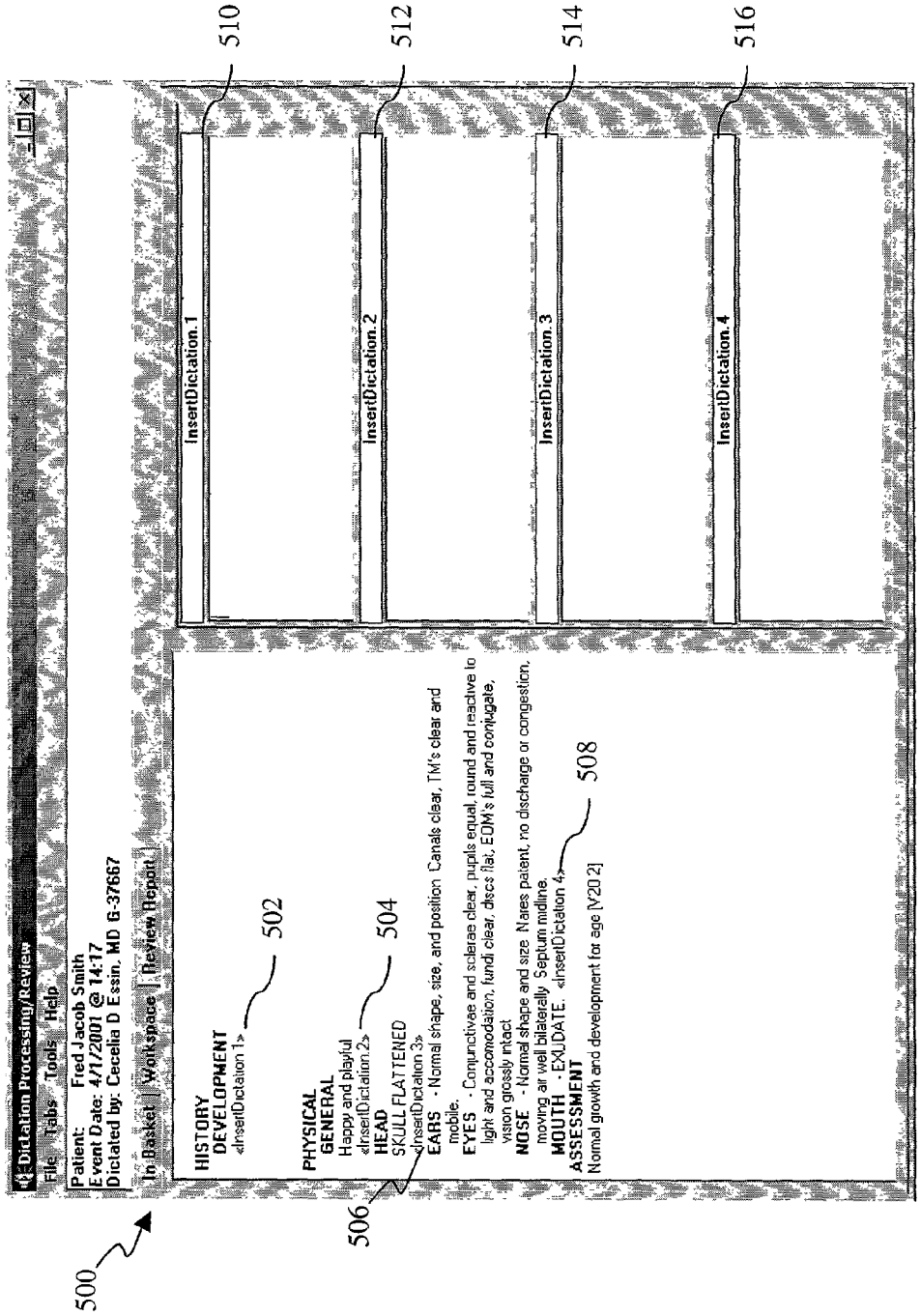
FIG. 14 is a screen capture illustrating a transcriber workspace with the document as authored and an individual text editor window for each insertion point in accordance with an exemplary embodiment of the present invention.

Returning to FIG. 11, a transcriber may then select a task 404 from the transcription queue. If the selected task is a new transcription or work that has been returned for correction 408 the described exemplary record management system displays a transcriber workspace 410 as illustrated in FIG. 14.

In the described exemplary embodiment the original document 500 may be displayed in the workspace with the dictation insertion points 502, 504, 506 and 508 highlighted. However, in the described exemplary embodiment the portions that were directly entered by the author are inviolate and can not be altered by the transcriber. The described exemplary record management system may assist the transcriber in processing the dictated material and linking each transcribed text with the proper insertion point within the XML document.

For example, an exemplary record management system may generate a separate dictation editor pane 510, 512, 514 and 516 for each dictation insertion point in the document. Each of the edit windows 510-516 in an exemplary transcriber workspace may be labeled with the name of the corresponding insertion point and preferably appear in the order that the insertion points were created.

Figure 15:
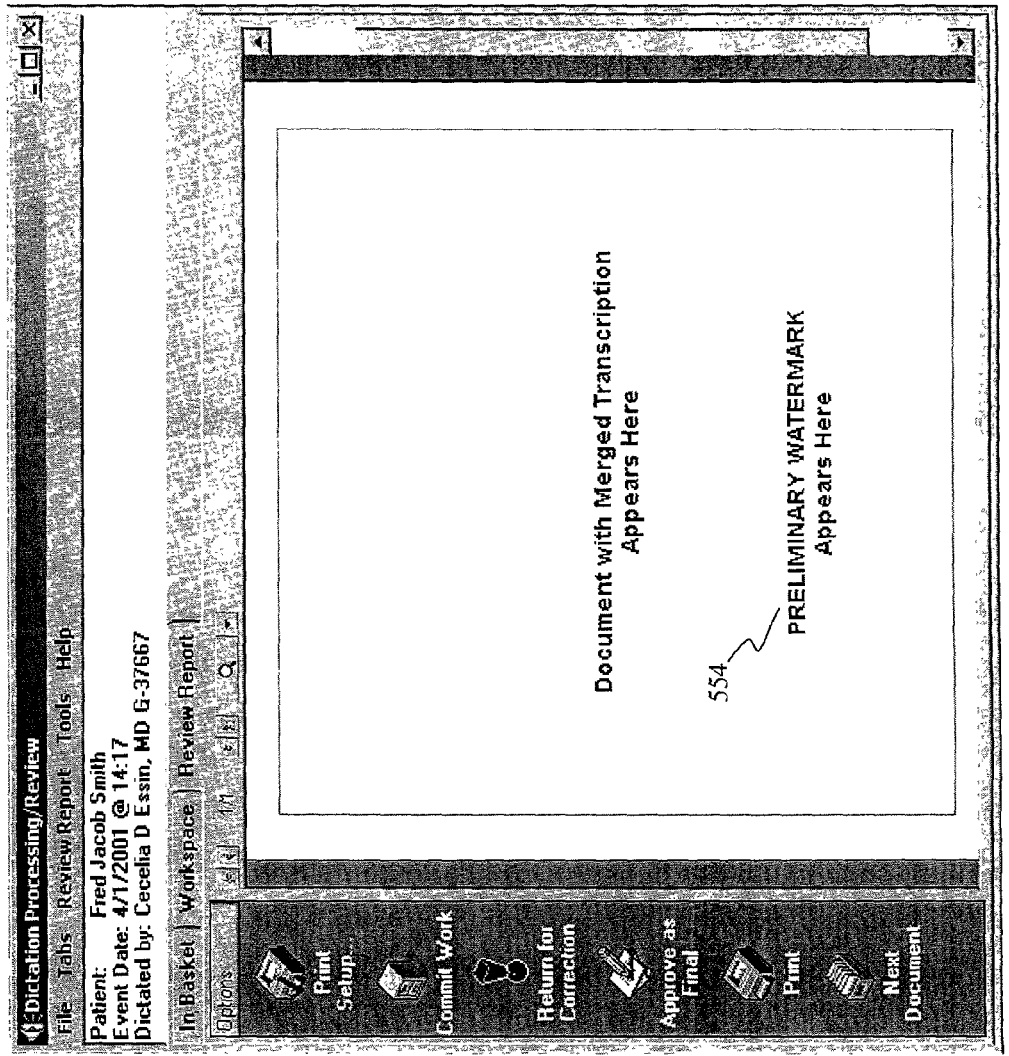
FIG. 15 is a screen capture of a document display interface for displaying documents in accordance with an exemplary embodiment of the present invention.

In accordance with an exemplary embodiment the edit windows may scroll into view as the transcriber tabs from one edit window to the next, allowing for uninterrupted typing. The described exemplary record management system may display completed work in a document display window 550 as illustrated in FIG. 15.

Returning to FIG. 11, in an exemplary embodiment the transcribed material is not initially merged with the authenticated preliminary document. Rather the content of each edit window is stored as a separate database record pending author approval 414. However, a rough draft may be generated that includes the transcribed material merged into the original document. This draft can be printed 416 or viewed on a document display window 412 but contains a preliminary watermark 554 (see FIG. 15) indicating that the document is a preliminary draft.

After review and approval by the author, the transcribed text may be merged and the XML document may be updated to produce the final document 420. The final document may be viewed in the document display window 422 and if desired may be printed 424 for hardcopy storage.

Figure 16:
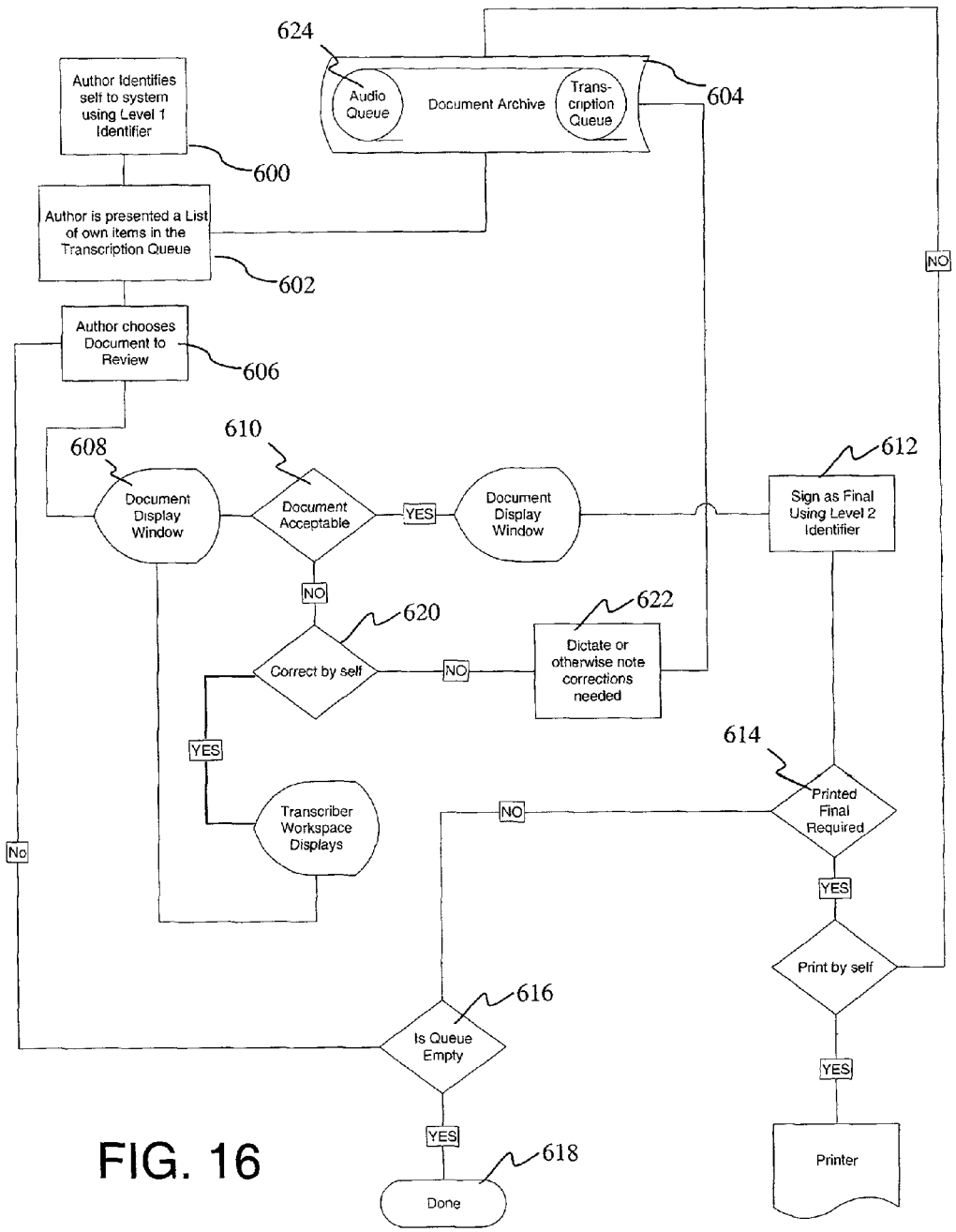
FIG. 16 a flowchart graphically illustrating an author review process for verifying/correcting transcribed documents in accordance with an exemplary embodiment of the present invention.

FIG. 16 graphically illustrates an exemplary review process that an author may use to approve or edit transcribed text. In accordance with an exemplary embodiment only the original author or an authorized designee can complete the document review process. In addition, the final XML document including the merged dictation retains the dictation insertion points, making it possible to determine which portions of the document were created directly by the author and which were prepared by the dictation and transcription process.

Figure 17:
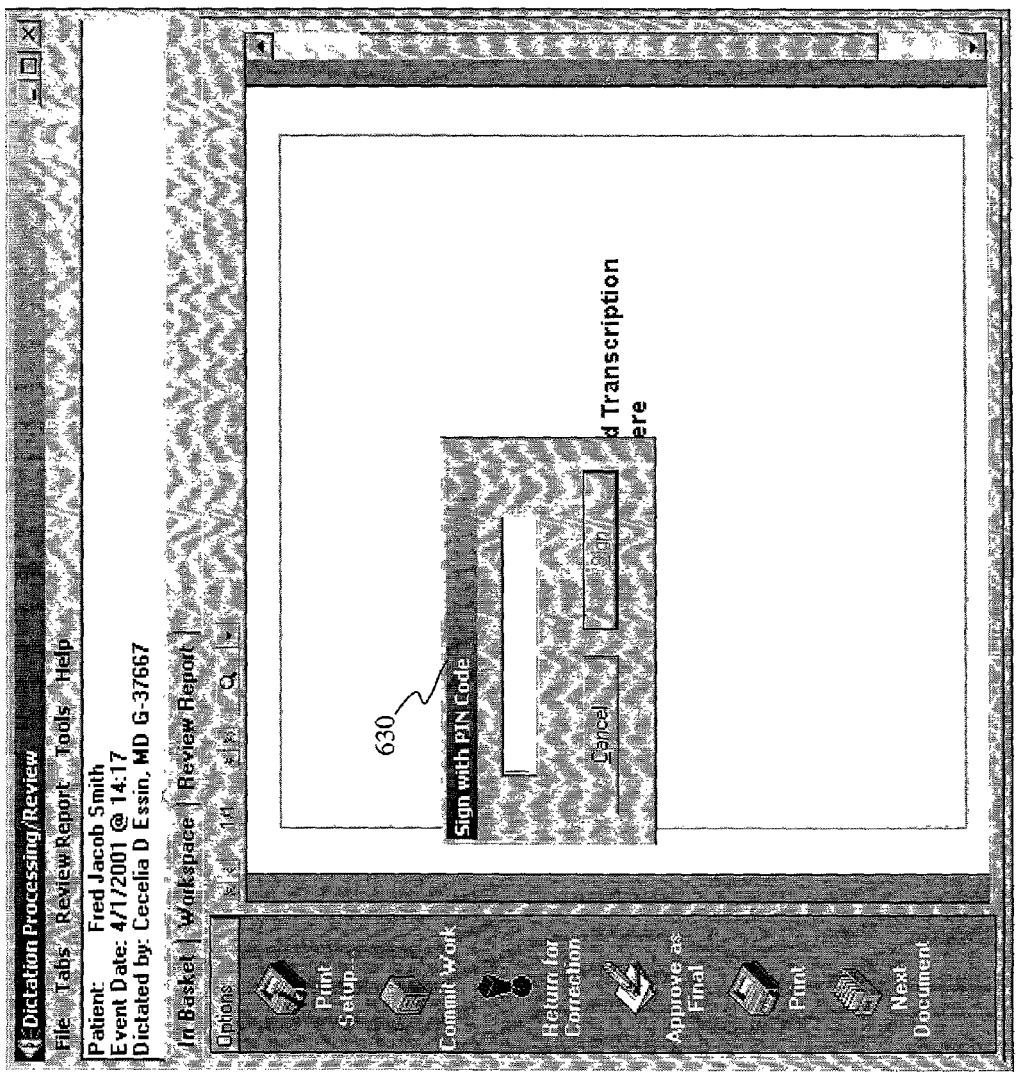
FIG. 17 is a screen capture of a dictation review interface wherein a user may digitally sign a document by entering a PIN code in accordance with an exemplary embodiment of the present invention.

Initially an author may log onto the described exemplary record management system 600 providing for example a login identification and a password. An exemplary record management system may display a list 602 of the author's items that are stored in the transcription queue 604. The author may select a document to review 606 which is then displayed in the document display window 608. If the document is acceptable 610 the author may digitally sign the document 612 by entering a personal identification code 630 as illustrated in FIG. 17. If a printed copy of the final document 614 is not required an exemplary system may determine if the authors transcription queue is empty 616. If so the author is done 618, if not the described exemplary system will again display a list of pending transcription jobs 606.

The described exemplary record management system may allow an author to correct the document under review if it is otherwise not acceptable 620. Alternatively, the author may dictate corrections to the document or otherwise note the needed corrections 622. The corrections may then be added to the audio queue 624 for input by a transcriber and further author review.

Figure 18:
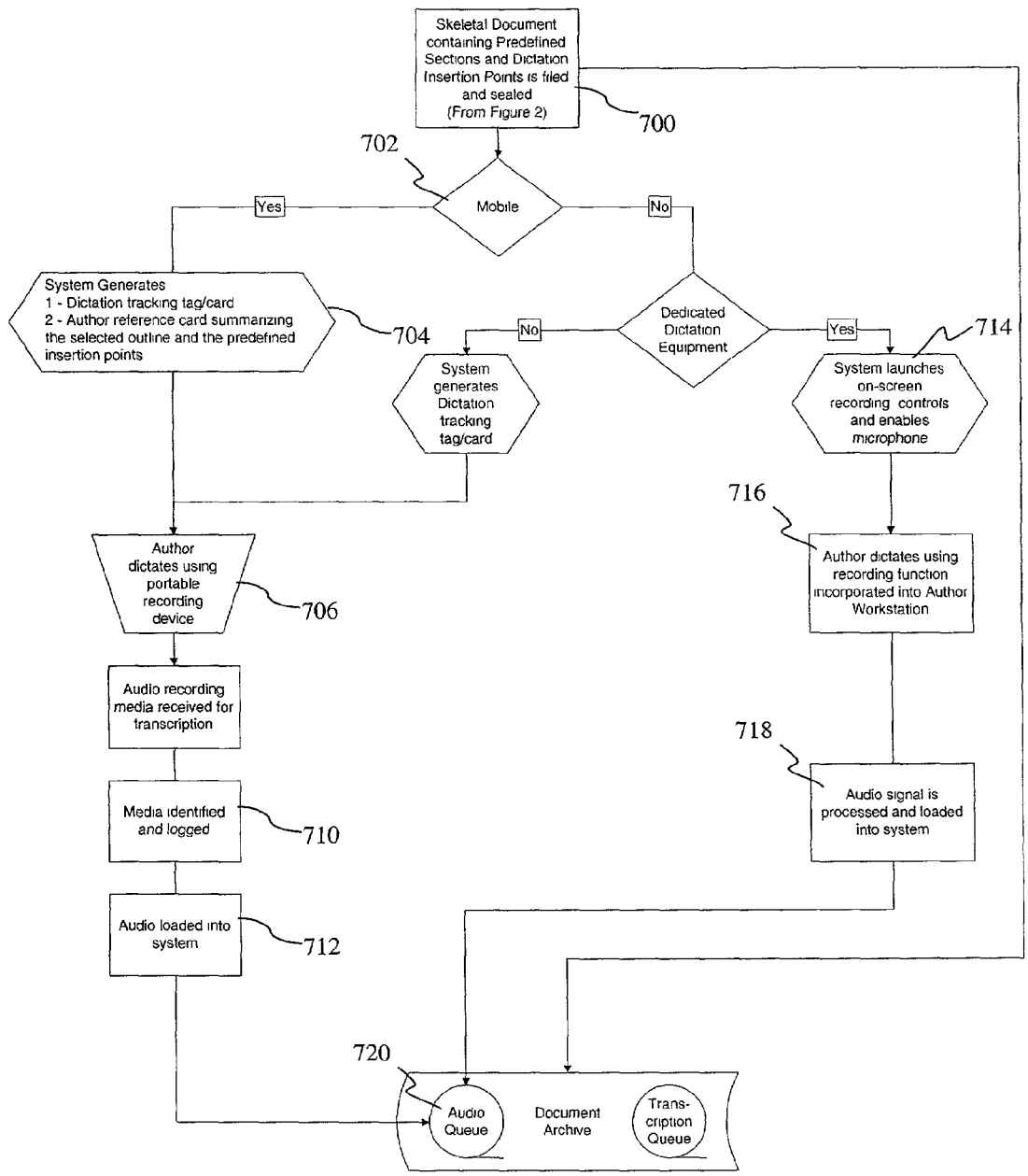
FIG. 18 is a flowchart graphically illustrating a dictation process in accordance with an exemplary embodiment of the present invention.

One of skill in the art will appreciate that a variety of techniques may be used to generate the narrative text and to insert that text into a final document. FIG. 18 graphically illustrates a flow diagram of an exemplary dictation process. In practice the narrative text may be generated after the skeletal outline containing the predefined dictation points has been filed and sealed 700 in the document archive.

A user may then use a fixed or mobile dictation station to generate the narrative text 702. If a mobile system or a fixed but non-dedicated system is used to generate the appropriate narratives, the described exemplary record management system may generate a dictation-tracking card that the user references when generating the text 704. The described exemplary tracking or identification card may be machine readable and may identify the author as well as the subject being documented, i.e. in this case the patient.

In addition the described exemplary record management system may generate a printed summary of the outline enumerating the predefined insertion points in the document which may then be attached to the tracking card. The user may then dictate using a portable recording device such as for example, a dictation machine with magnetic storage media or a hand held computing device optionally equipped with voice recognition software 706, in accordance with the attached document summary.

Figure 11:
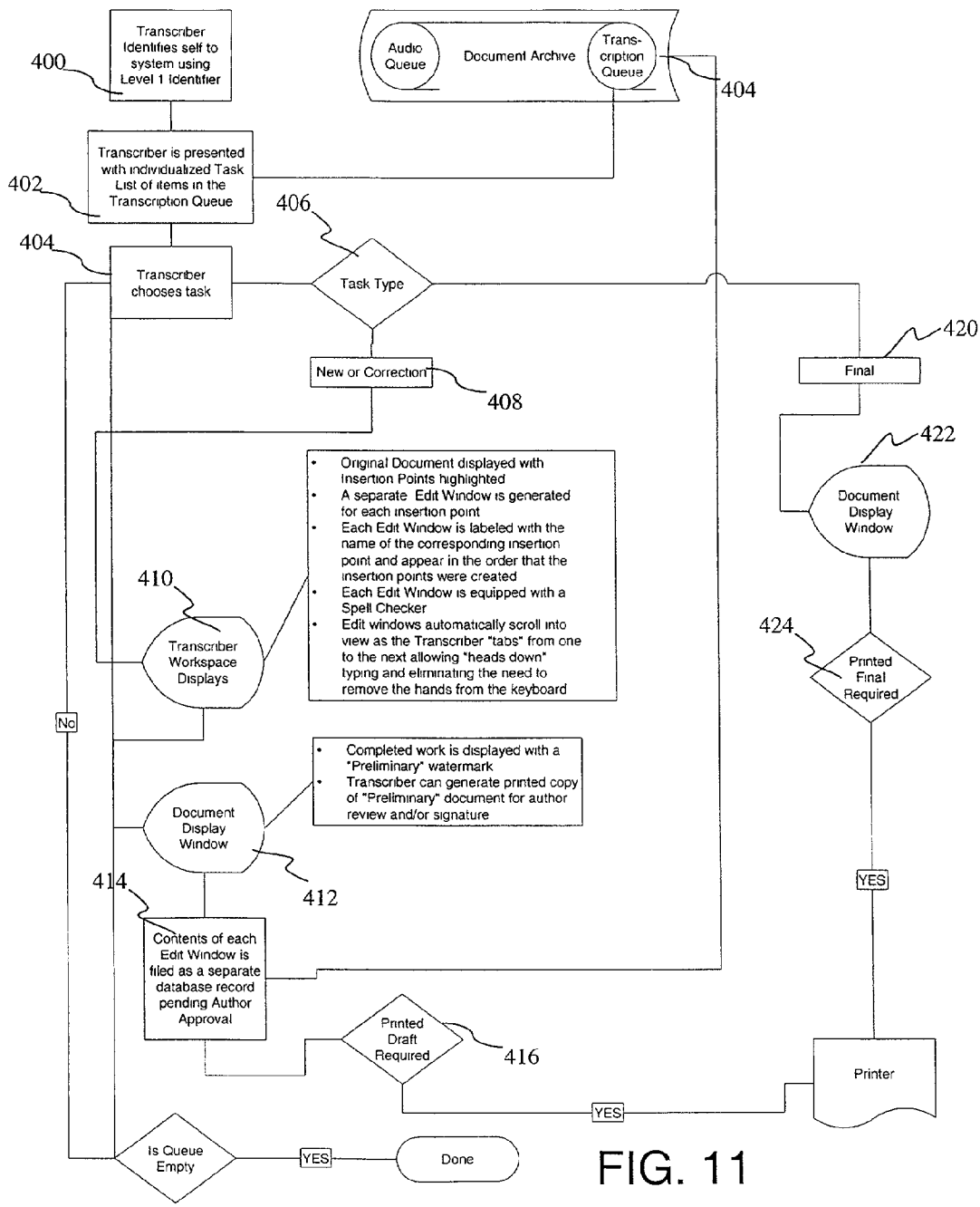
FIG. 11 is a flowchart graphically illustrating a transcription process for transcribing narrative information items in accordance with an exemplary embodiment of the present invention.

The appropriate storage media may then be identified and logged 710 and loaded into the system 712 for subsequent transcription as previously described with respect to FIG. 11. The transcribed document may then be entered into the audio queue for user review.

If the user is utilizing a fixed, dedicated dictation station, the described exemplary record management system may display on-screen recording controls and activate a microphone for audio input. The user may then dictate the narrative portions of the document using a recording function incorporated into the dictation workstation 716. The audio recording may again be processed 718 and loaded into the audio queue 720 of the document archive.

Figure 19:
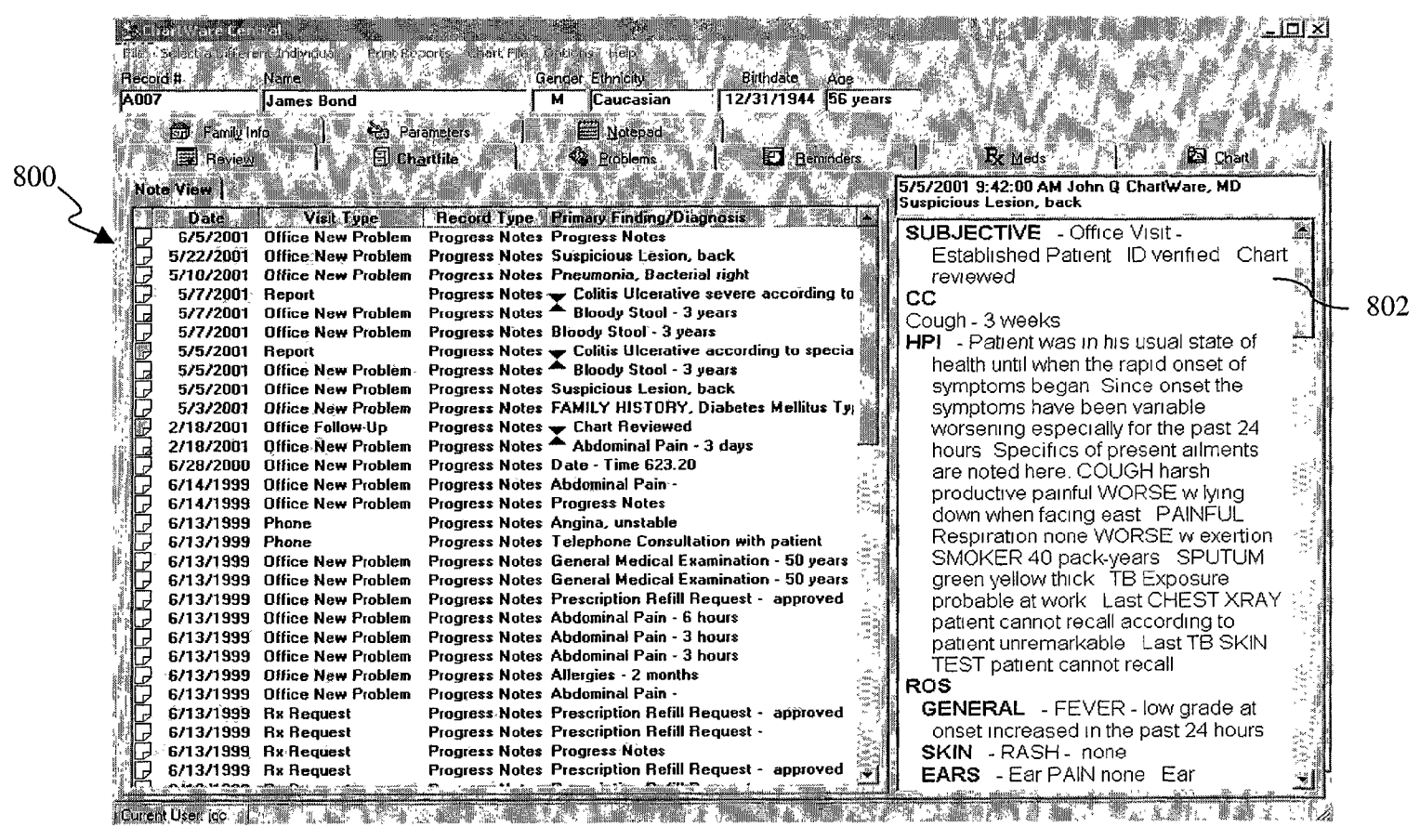

Referring to FIG. 19, the described exemplary record management system allows for the creation of a user specific outline for any of a variety of diverse users. In accordance with an exemplary embodiment, each new document may differ both in content and the number of items included in the outline. However, documents created in accordance with the described exemplary process conform to the same document type definition and to the extensible markup language specification. Thus, the final outlines stored in the outline database are compatible and maintain their internal organization and structure. Therefore, a patients entire examination history 800 may be displayed for example in a chronological list along with a display panel 802 that allows the selected outline to be reviewed. In addition, the coded information within each document may be searched an analyzed for any of a variety of purposes.

Although an exemplary record management system has been described, it should not be construed to limit the scope of the appended claims. Those skilled in the art will understand that various modifications may be made to the described embodiment and that numerous other configurations are capable of achieving this same result.

Moreover, to those skilled in the various arts, the invention itself herein will suggest solutions to other tasks and adaptations for other applications that require contemporaneous authenticated documentation and that may include the use of dictation and transcription to generate a portion of the document content. For example, the described exemplary record management system may be adapted for use in the law enforcement environment wherein an officer may directly enter certain quantitative observations that result for example from an accident investigation.

The qualitative information may again be signed and sealed in a substantially tamper proof database. The officer may further identify dictation insertion points in the accident investigation outline. The officer may generate the corresponding narrative by dictating appropriate passages into a hand held device optionally having voice recognition software, that automatically stores a transcribed version of the dictated text in the audio queue for the officers review and merger into a final document upon approval.

It is the applicants intention to cover by claims all such uses of the invention and those changes and modifications which could be made to the embodiments of the invention herein chosen for the purpose of disclosure without departing from the spirit and scope of the invention.

What is claimed is:

1. An electronic medical record management system for generating an electronic medical document based on a specific context from among a plurality of contexts within which an event may be documented, the system comprising:
    means for providing one or more headings and a selection of available subheadings corresponding to each of the one or more headings;
    means for receiving requests from one or more users to enter content under one or more of the selection of available subheadings corresponding to at least one of the one or more headings;
    means for converting each of the one or more available subheadings for which a request to enter content has been received into a corresponding one of one or more selected subheadings;
    means for receiving requests from the one or more users to associate at least one of a plurality of contexts with the one or more selected subheadings and headings; and
    means for generating an electronic medical document including the entered content and the corresponding selected subheadings and headings that are associated with a specific context from among the plurality of contexts.

2. The record management system of claim 1 further comprising means for directly entering quantitative information into said electronic document.

3. The record management system of claim 2 further comprising means for generating a digitally signed message digest when said electronic document is created to provide for detection of unauthorized alteration of said electronic document.

4. The record management system of claim 1 further comprising means for creating dictation insertion points within said electronic document.

5. The record management system of claim 4 further comprising means for uniquely identifying said dictation insertion points.

6. The record management system of claim 4 further comprising means for displaying said electronic document in a workspace having a plurality of window panes, wherein said workspace displays original content of said electronic document in one of said plurality of window panes with the dictation insertion points highlighted.

7. The record management system of claim 4 means for merging transcribed material with said electronic document.

8. The record management system of claim 7 further comprising means for displaying content of said merged document, wherein non-approved transcribed material is marked with a preliminary watermark.

9. The record management system of claim 1 further comprising speech recognition means for generating a portion of content of said electronic document.

10. The record management system of claim 1 further comprising means for defining a meaning of a term as a literal constant.

11. The record management system of claim 1 further comprising means for defining a meaning of a term as a database query.

12. The record management system of claim 1 further comprising means for defining a meaning of a term as a pointer to an external lexicon or nomenclature.

13. The record management system of claim 1 further comprising means for modifying at least a portion of said one or more headings, said selection of available subheadings, or said one or more selected subheadings.

14. The record management system of claim 13 wherein said means for modifying at least a portion of said one or more headings, said selection of available subheadings, or said one or more selected subheadings comprises means for modifying at least a portion of said one or more headings, said selection of available subheadings, or said one or more selected subheadings in accordance with data entry choices.

15. The record management system of claim 13 wherein said means for modifying at least a portion of said one or more headings, said selection of available subheadings, or said one or more selected subheadings comprises means for merging at least a portion of stored electronic documents into the electronic document currently in use.

16. The record management system of claim 13 wherein the means for modifying at least a portion of said one or more headings, said selection of available subheadings, or said one or more selected subheadings comprises programming logic stored within said electronic document that modifies at least a portion of said one or more headings, said selection of available subheadings, or said one or more selected subheadings in accordance with content of the electronic document at a time the logic rule is invoked.

17. The record management system of claim 13, wherein the means for modifying at least a portion of said one or more headings, said selection of available subheadings, or said one or more selected subheadings comprises programming logic stored within said electronic document that modifies the information displayed within a user-interface and the behavior of the user-interface or the information that is inserted into the document being created in accordance with content of the electronic document at a time the logic rule is invoked.

18. The record management system of claim 1 further comprising means for assigning authors to one or more organizational groups or subgroups.

19. The record management system of claim 18 further comprising means for creating virtual queues for assigning a stenographer to transcribe for specific organizational groups.

20. The record management system of claim 1 further comprising means for approving said merged transcribed material.

21. The record management system of claim 1 wherein the content of said one or more selected subheadings comprises context-dependent pointers to metadata for linking said one or more selected subheadings to one or more coding schemes.

22. The record management system of claim 21 wherein said coding scheme comprises a uni-axial coding scheme.

23. The record management system of claim 21 wherein said coding scheme is a multi-axial coding scheme.

24. A method for managing electronic medical records by generating an electronic medical document based on a specific context from among a plurality of contexts within which an event may be documented, the method comprising:

providing one or more headings and a selection of available subheadings corresponding to each of the one or more headings;

receiving user requests to enter content under one or more of the selection of available subheadings corresponding to at least one of the one or more headings;

converting each of the one or more available subheadings is for which a user request to enter content has been received into a corresponding one of one or more selected subheadings;

receiving a user request to associate at least one of a plurality of contexts with the one or more selected subheadings and headings; and generating an electronic medical document including the entered content and the corresponding selected subheadings and headings that are associated with a specific context from among the plurality of contexts.

25. The method of claim 24 wherein receiving user requests to enter content under one or more of the selection of available subheadings comprises receiving user requests to associate pointers with the one or more available subheadings to metadata for linking the one or more available subheadings to one or more coding schemes.

26. The method of claim 24 further comprising directly entering quantitative information into said electronic document.

27. The method of claim 26 further comprising generating a digitally signed message digest when said electronic document is created to provide for detection of unauthorized alteration of said electronic document.

28. The method of claim 24 further creating dictation insertion points within said electronic document.

29. A method for managing electronic medical records by generating an electronic medical document based on at least one of a plurality of contexts within which an event may be documented, the method comprising:

providing one or more headings and a selection of available subheadings corresponding to each of the one or more headings;

receiving a user request to enter content under one or more of the selection of available subheadings corresponding to at least one of the one or more headings;

converting each of the one or more available subheadings for which a user request to enter content has been received into a corresponding one of one or more selected subheadings;

associating pointers with the one or more selected subheadings to metadata for linking the one or more selected subheadings to one or more coding schemes that are context specific;

creating dictation insertion points; and generating an electronic medical document including the entered content and the corresponding selected subheadings, headings, and dictation insertion points that are associated with pointers corresponding to at least one of the one or more context specific coding schemes.

30. An electronic medical record management system for generating an electronic medical document based on a specific context from among a plurality of contexts within which an event may be documented, the system comprising a server coupled to one or more workstations, wherein a computing device of the server or one of the one or more workstations:

provides one or more headings and a selection of available subheadings corresponding to each of the one or more headings;

receives input signals from one or more authors to enter content for association with one or more of the selection of available subheadings corresponding to at least one of the one or more headings;

converts each of the one or more available subheadings for which an input signal to enter content has been received into a corresponding one of one or more selected subheadings to be associated with a position within a structural hierarchy;

receives input signals from the one or more authors to associate one or more of a plurality of contexts with the entered content and/or selected subheadings and corresponding headings;

defines outlines for presenting the content to the one or more authors in an electronic medical document; and generates the electronic medical document including the content and the associated selected subheadings and headings that are associated with a specific context from among the plurality of contexts.

31. The record management system of claim wherein the computing device further enters quantitative information into said electronic document in a way that components of the quantitative information link to a terminology lexicon and the components are embedded in the electronic document as discrete elements that are automatically tagged.

32. The record management system of claim 31 wherein the components are additional descriptors that provide information necessary to correctly interpret or process the quantitative information.

33. The record management system of claim 31 wherein the quantitative information includes units of measure, duration, and anatomical location.

34. The record management system of claim 30 wherein the computing device further generates a digitally signed message digest when the electronic document is created to provide for detection of unauthorized alteration of the electronic document.

35. The record management system of claim 30, wherein the computing device further receives input signals from the one or more authors to create insertion points within said electronic document and to associate the insertion points with individual dictation fragments contained within an audio recording.

36. The record management system of claim 30, wherein the computing device further displays said electronic document in a workspace having a plurality of editor window panes that have a visible and logical association with the individually numbered insertion points that are present within the document, wherein said workspace displays the content of said electronic document in an additional window pane with the dictation insertion points highlighted.

37. The record management system of claim 30, wherein at least one of the one or more workstations comprises a portable electronic device.

38. An electronic medical record management system for generating an electronic medical document based on a specific context from among a plurality of contexts within which an event may be documented, the system comprising:

means for defining snippets that constitute a semantic category;

means for linking the snippets to items of an outline, the items including one or more headings existing in a plurality of contexts, and a selection of available subheadings corresponding to each of the one or more headings;

means for receiving requests from an author to enter content under one or more of the selection of available subheadings corresponding to at least one of the one or more headings;

means for converting each of the one or more available subheadings for which a request to enter content has been received into a corresponding one of one or more selected subheadings;

means for receiving requests from the author to associate at least one of the plurality of contexts with the one or more selected subheadings and headings;

means for creating links between the snippets such that a meaning of one item of the items linked to a first snippet of the snippets can be modified or extended by a second snippet of the snippets to which it is linked; and means for generating an electronic medical document with outline fragments that can be composed by pre-definition or dynamically, the electronic medical document including the entered content and the corresponding selected subheadings and headings that are associated with a specific context from among the plurality of contexts.

39. The electronic record management system of claim 38 further comprising:

means for selecting an outline or an outline fragment; and means for inserting a dictation annotation into the selected outline or selected outline fragment at a point within the selected outline or selected outline fragment that is of the author's choosing.

* * * * *

UNITED STATES PATENT AND TRADEMARK OFFICE
CERTIFICATE OF CORRECTION

| | | |
|---|---|---|
| PATENT NO. | : 7,802,183 B1 | |
| APPLICATION NO. | : 10/150709 | |
| DATED | : September 21, 2010 | |
| INVENTOR(S) | : Daniel J. Essin | |

It is certified that error appears in the above-identified patent and that said Letters Patent is hereby corrected as shown below:

In the Claims

Column 16, Claim 24, line 1     Delete "is"

Column 17, Claim 31, line 14    After "claim" Insert -- 30 --

Signed and Sealed this
Thirteenth Day of September, 2011

David J. Kappos
*Director of the United States Patent and Trademark Office*